(12) United States Patent
Alenfalk et al.

(10) Patent No.: US 7,863,265 B2
(45) Date of Patent: *Jan. 4, 2011

(54) 2-AZETIDINONE DERIVATIVES AND THEIR USE AS CHOLESTEROL ABSORPTION INHIBITORS FOR THE TREATMENT OF HYPERLIPIDAEMIA

(75) Inventors: Susanne Alenfalk, Molndal (SE); Mikael Dahlstrom, Molndal (SE); Fana Hunegnaw, Molndal (SE); Staffan Karlsson, Molndal (SE); Malin Lemurell, Molndal (SE); Ann-Margret Lindqvist, Molndal (SE); Tore Skjaret, Molndal (SE); Ingemar Starke, Molndal (SE)

(73) Assignee: AstraZeneca AB, Sodertalje (SE)

( * ) Notice: Subject to any disclaimer, the term of this patent is extended or adjusted under 35 U.S.C. 154(b) by 466 days.

This patent is subject to a terminal disclaimer.

(21) Appl. No.: 11/993,033

(22) PCT Filed: Jun. 19, 2006

(86) PCT No.: PCT/SE2006/000741

§ 371 (c)(1), (2), (4) Date: Dec. 19, 2007

(87) PCT Pub. No.: WO2006/137782

PCT Pub. Date: Dec. 28, 2006

(65) Prior Publication Data

US 2010/0216759 A1 Aug. 26, 2010

(30) Foreign Application Priority Data

Jun. 20, 2005 (SE) .................................. 0501425

(51) Int. Cl.
*A61K 31/397* (2006.01)
*C07D 205/08* (2006.01)
*C07D 413/12* (2006.01)
*C07D 319/06* (2006.01)
*A61P 3/06* (2006.01)

(52) U.S. Cl. .................. 514/210.02; 540/360; 548/230; 549/375

(58) Field of Classification Search ................. 540/360; 514/210.02

See application file for complete search history.

(56) References Cited

U.S. PATENT DOCUMENTS

| 5,633,246 | A | 5/1997 | McKittrick et al. |
| 5,661,145 | A | 8/1997 | Davis |
| 5,744,467 | A | 4/1998 | McKittrick et al. |
| 7,235,543 | B2 | 6/2007 | Burnett et al. |
| 7,368,562 | B2 | 5/2008 | Burnett et al. |
| 7,470,678 | B2* | 12/2008 | Starke et al. ........... 514/210.09 |
| 2003/0119428 | A1 | 6/2003 | Davis et al. |
| 2003/0119757 | A1 | 6/2003 | Davis |
| 2004/0018060 | A1 | 1/2004 | Knezek et al. |
| 2004/0018061 | A1 | 1/2004 | Jansson |
| 2004/0254369 | A1 | 12/2004 | Framroze |
| 2005/0096307 | A1 | 5/2005 | Graziano |
| 2005/0267049 | A1 | 12/2005 | Goulet et al. |
| 2006/0046996 | A1 | 3/2006 | Aoki et al. |
| 2006/0069080 | A1 | 3/2006 | Veltri |
| 2007/0049748 | A1 | 3/2007 | Uppala et al. |
| 2007/0078098 | A1 | 4/2007 | DeVita et al. |
| 2007/0129540 | A1 | 6/2007 | Framroze |
| 2007/0142304 | A1* | 6/2007 | Alenfalk et al. ................ 514/19 |

(Continued)

FOREIGN PATENT DOCUMENTS

| EP | 1413331 | 9/2001 |
| EP | 0792264 | 2/2002 |
| EP | 1362855 | 11/2003 |
| WO | 2004081002 | 5/1996 |
| WO | 03026643 | 4/2003 |
| WO | 2004005247 | 1/2004 |

(Continued)

OTHER PUBLICATIONS

Office Action dated May 3, 2010 received in copending U.S. Appl. No. 10/596,731.

(Continued)

*Primary Examiner*—Mark L Berch
(74) *Attorney, Agent, or Firm*—Pepper Hamilton LLP

(57) ABSTRACT

Compounds of formula (I) (wherein variable groups are as defined within) pharmaceutically acceptable salts, solvates, solvates of such salts and prodrugs thereof and their use as cholesterol absorption inhibitors for the treatment of hyperlipidaemia are described. Processes for their manufacture and pharmaceutical compositions containing them are also described.

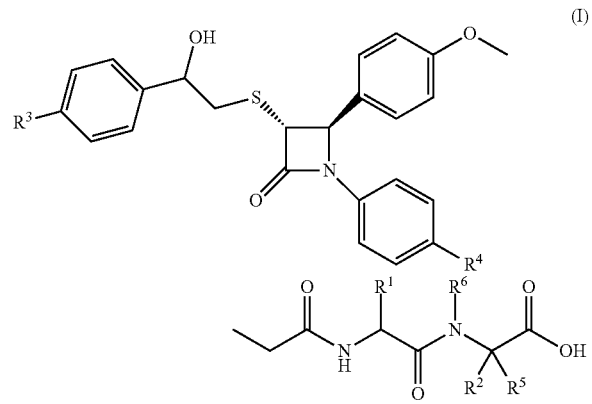

2 Claims, No Drawings

U.S. PATENT DOCUMENTS

| | | | |
|---|---|---|---|
| 2007/0155674 A1 | 7/2007 | Burnett et al. | |
| 2007/0155675 A1 | 7/2007 | Burnett et al. | |
| 2008/0064676 A1* | 3/2008 | Alenfalk et al. | 514/210.02 |
| 2008/0070890 A1* | 3/2008 | Burnett et al. | 514/210.05 |
| 2009/0069285 A1* | 3/2009 | Lemurell et al. | 514/210.02 |
| 2010/0048529 A1* | 2/2010 | Dahlstrom et al. | 514/210.02 |
| 2010/0048530 A1* | 2/2010 | Dahlstrom et al. | 514/210.15 |
| 2010/0099657 A2* | 4/2010 | Alenfalk et al. | 514/210.02 |
| 2010/0125059 A1* | 5/2010 | Nakano et al. | 514/210.02 |
| 2010/0137273 A1* | 6/2010 | Alenfalk et al. | 514/210.02 |
| 2010/0152156 A1* | 6/2010 | Dahlstrom et al. | 514/210.02 |
| 2010/0168075 A1* | 7/2010 | Dahlstrom et al. | 514/210.02 |

FOREIGN PATENT DOCUMENTS

| | | |
|---|---|---|
| WO | 2004043456 | 5/2004 |
| WO | 2004043457 | 5/2004 |
| WO | 2004099132 | 11/2004 |
| WO | 2004107958 | 12/2004 |
| WO | 2005000353 | 1/2005 |
| WO | 2005021495 | 3/2005 |
| WO | 2005021497 | 3/2005 |
| WO | 2005042692 | 5/2005 |
| WO | 2005044256 | 5/2005 |
| WO | 2005047248 | 5/2005 |
| WO | 2005049592 | 6/2005 |
| WO | 2005058316 | 6/2005 |
| WO | 2005033100 | 7/2005 |
| WO | 2005061451 | 7/2005 |
| WO | 2005061452 | 7/2005 |
| WO | 2005062824 | 7/2005 |
| WO | 2005062897 | 7/2005 |
| WO | 2005066120 | 7/2005 |
| WO | 2005067903 | 7/2005 |
| WO | 2005069900 | 8/2005 |
| WO | 2005113495 | 12/2005 |
| WO | 2005113496 | 12/2005 |
| WO | 2006017257 | 2/2006 |
| WO | 2006060808 | 6/2006 |
| WO | 2006068990 | 6/2006 |
| WO | 2006072957 | 7/2006 |
| WO | 2006086562 | 8/2006 |
| WO | 2006102674 | 9/2006 |
| WO | 2006107936 | 10/2006 |
| WO | 2006116499 | 11/2006 |
| WO | 2006121861 | 11/2006 |
| WO | 2006122186 | 11/2006 |
| WO | 2006122216 | 11/2006 |
| WO | 2006124713 | 11/2006 |
| WO | 2006127893 | 11/2006 |
| WO | 2006134604 | 12/2006 |
| WO | 2006137080 | 12/2006 |
| WO | 2006137782 | 12/2006 |
| WO | 2006137792 | 12/2006 |
| WO | 2006137793 | 12/2006 |
| WO | 2006137794 | 12/2006 |
| WO | 2006137795 | 12/2006 |
| WO | 2006137796 | 12/2006 |
| WO | 2006137797 | 12/2006 |
| WO | 2006138163 | 12/2006 |
| WO | 2007003365 | 1/2007 |
| WO | 2007008529 | 1/2007 |
| WO | 2007008541 | 1/2007 |
| WO | 2007015161 | 2/2007 |
| WO | 2007016643 | 2/2007 |
| WO | 2007017705 | 2/2007 |
| WO | 2007030721 | 3/2007 |
| WO | 2007058335 | 5/2007 |
| WO | 2007059871 | 5/2007 |
| WO | 2007072088 | 6/2007 |
| WO | 2007075702 | 7/2007 |

OTHER PUBLICATIONS

Office Ation dated Jul. 15, 2009 received in copending U.S. Appl. No. 10/596,725.
Office Action dated Sep. 17, 2009 received in copending U.S. Appl. No. 10/596,731.
McKittrick, B.A., et al., "Synthesis of C3 Heteroatom-substituted Azetidinones that Display Potent Cholesterol Absorption Inhibitory Activity", J. Med. Chem., 1998, 41:752-759.
Notice of allowance dated Jul. 31, 2008 for U.S. Appl. No. 10/519,897.
Office Action dated Feb. 28, 2008 for U.S. Appl. No. 10/519,897.
Notice of allowance dated Aug. 28, 2007 for U.S. Appl. No. 10/519,897.
Office Action dated May 1, 2007 for U.S. Appl. No. 10/519,897.
Ritter et al., "Heterocyclic ring scaffolds as small-molecule cholesterol absorption inhibitors," Org Biomol Chem (2005) 3:3514-3523.
Clader et al., "2-Azetidinone Cholesterol Absorption Inhibitors: Structure-Activity Relationships on the HeterocyclicNucleus," J. Med Chem (1996) 39:3684-3693.
McKittrick et al., Stereoselective synthesis and biological activity of cis azetidinones as cholesterol absorptioninhibitors, Bioorganic & Medicinal Chemistry Letters (1996) 6(16):1947-1950.
Burnett et al., "2-Azetidinones as Inhibitors of Cholesterol Absorption," J. Med Chem (1994) 12:1733-1736.
Castaner et al., "Ezetimibe Hypolipidemic, Cholesterol absorption inhibitor," Drugs of the Future (2000) 25(7):679-685.
Vaccaro et al., "Sugar-substituted 2-azetidinone cholesterol absorption inhibitors: Enhanced potency by modification ofthe sugar," Bioorganic & Medicinal Chemistry Letters (1998) 8:313-318.
Fu et al., "Process for preparing Ezetimibe intermediate by an acid enhanced chemo- and enantioselective CBScatalyzed ketone reduction," Tetrahedron Letters (2003) 44:801-804.
Kirkup et al., "(I)-SCH 57939: synthesis and pharmacological properties of a potent, metabolically stable cholesterolabsorption inhibitor," Bioorganic & Medicinal Chemistry Letters (1996) 6(17):2069-2072.
Rosenblum et al., "Discovery of 1-(4-fluorophenyl)-(3R)[3-(4-fluorophenyl)-(3S)-hydroxypropyl]-(4S)-(4-hydroxyphenyl)-2-azetidinone (SCH 58235): a designed, potent, orally active inhibitor of cholesterol absorption.," J. Med Chem (1998) 41:973-980.
Wu et al., "A Novel One-Step Diastereo- and Enantioselective Formation of trans-Azetidinones and Its Application tothe Total Synthesis of Cholesterol Absorption Inhibitors," J. Org. Chem (1999) 64:3714-3718.
Dugar et al., "Gamma-lactams and related compounds as cholesterol absorption inhibitors: homologs of the beta-lactam cholesterol absorption inhibitor SCH 48461," Bioorganic & Medicinal Letters (1995) 5(24):2947-2952.
Mounsey et al., "Diet may slow progression of diabetic nephropathy," The Journal of Family Practice (2003) 52(9):672-673.
Sobieszczyk et al., "Acute pulmonary embolism: don't ignore the platelet," Circulation (2002) 106(14):1748-1749.
van Heek et al., "Comparison of the activity and disposition of the novel cholesterol absorption inhibitor, SCH58235, and its glucuronide, SCH60663," Br. J. Pharmacol (2000) 129(8):1748-1754.
Yang et al., "Allelic Variants in Long-QT Disease Genes in Patients With Drug-Associated Torsades de Pointes,"Circulation (2002) 105(16):1943-1948.
Zaks et al., Enzymatic glucuronidation of a novel cholesterol absorption inhibitor, Sch 58235, Appl BiochemBiotechnol. (1998) 73(2-3):205-214.
Clader "The discovery of ezetimibe: a view from outside the receptor," J Med Chem (2004 47(1):1-9.
Altmann et al., "Niemann-pick C1 like 1 protein is critical for intestinal cholesterol absorption," Science(2004) 303:1201-1204.
Carcia-Calvo et al., "The target of ezetimibe is Niemann-Pick C1-Like 1 (NPC1L1)," PNAS (2005) 102(23):8132-8137.
Journal of the American College of Cardiology (2000) 35(1):252A.

Kvaerno et al., "Synthesis and in vitro evaluation of inhibitors of intestinal cholesterol absorption," J Med Chem (2005) 48(19):6035-6053.

Burnett "Beta-lactam cholesterol absorption inhibitors," Curr Med Chem (2004) 11:1873-1887.

Seedorf et al., "Cholesterol absorption inhibitor ezetimibe blocks uptake of oxidized LDL in human macrophages," Biochem Biophys Research Commun (2004) 320(4):1337-1341.

Kvaerno et al., "An in vitro assay for evaluation of small-molecule inhibitors of cholesterol absorption," (2004) 43 (35):4653-4656.

Clader "Ezetimibe and other azetidinone cholesterol absorption inhibitors," Curr Topics in Med Chem (2005) 5 (3):243-256.

Notice of Allowance and Fee(s) Due received in copending U.S. Appl. No. 10/596,731 dated May 27, 2010.

Non Final Office Action received in copending U.S. Appl. No. 11/993,466 dated Jun. 9, 2010.

Non Final Office Action received in copending U.S. Appl. No. 11/993,463 dated Jun. 7, 2010.

Office Action dated Jun. 4, 2010 received in copending U.S. Appl. No. 11/993,484.

Office Action dated Jun. 9, 2010 received in copending U.S. Appl. No. 11/993,479.

Office Action dated Jun. 9, 2010 received in copending U.S. Appl. No. 11/993,475.

Office Action dated Jun. 10, 2010 received in copending U.S. Appl. No. 11/993,470.

Notice of Allowance dated Oct. 12, 2010 received in copending U.S. Appl. No. 11/993,466.

Notice of Allowance dated Nov. 10, 2010 received in copending U.S. Appl. No. 11/993,463.

* cited by examiner

2-AZETIDINONE DERIVATIVES AND THEIR USE AS CHOLESTEROL ABSORPTION INHIBITORS FOR THE TREATMENT OF HYPERLIPIDAEMIA

CROSS-REFERENCE TO RELATED APPLICATIONS

This application is the U.S. National Stage filing of International Application Serial No. PCT/SE2006/000741 filed Jun. 19, 2006, which claims priority to Swedish Application Serial No. 0501425-3 filed Jun. 20, 2005, each of which is incorporated herein by reference in its entirety.

This invention relates to 2-azetidinone derivatives, or pharmaceutically acceptable salts, solvates, solvates of such salts and prodrugs thereof. These 2-azetidinones possess cholesterol absorption inhibitory activity and are accordingly of value in the treatment of disease states associated with hyperlipidaemic conditions. They are therefore useful in methods of treatment of a warm-blooded animal, such as man. The invention also relates to processes for the manufacture of said 2-azetidinone derivatives, to pharmaceutical compositions containing them and to their use in the manufacture of medicaments to inhibit cholesterol absorption in a warm-blooded animal, such as man. A further aspect of this invention relates to the use of the compounds of the invention in the treatment of dyslipidemic conditions.

Atherosclerotic coronary artery disease is a major cause of death and morbidity in the western world as well as a significant drain on healthcare resources. It is well-known that hyperlipidaemic conditions associated with elevated concentrations of total cholesterol and low density lipoprotein (LDL) cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930-1938 and "Diabetes and Cardiovascular Disease: A Statement for Healthcare Professionals from the American Heart Association" Grundy S, Benjamin I., Burke G., et al; Circulation, 1999, 100, 1134-46).

The concentration of plasma cholesterol depends on the integrated balance of endogenous and exogenous pathways of cholesterol metabolism. In the endogenous pathway, cholesterol is synthesized by the liver and extra hepatic tissues and enters the circulation as lipoproteins or is secreted into bile. In the exogenous pathway cholesterol from dietary and biliary sources is absorbed in the intestine and enters the circulation as component of chylomicrons. Alteration of either pathway will affect the plasma concentration of cholesterol.

The precise mechanism by which cholesterol is absorbed from the intestine is however not clear. The original hypothesis has been that cholesterol is crossing the intestine by unspecific diffusion. But more recent studies are suggesting that there are specific transporters involved in the intestinal cholesterol absorption. (See for instance New molecular targets for cholesterol-lowering therapy Izzat, N. N., Deshazer, M. E. and Loose-Mitchell D. S. JPET 293:315-320, 2000.)

A clear association between reduction of total cholesterol and (LDL) cholesterol and decreased instance of coronary artery disease has been established, and several classes of pharmaceutical agents are used to control serum cholesterol. There major options to regulate plasma cholesterol include (i) blocking the synthesis of cholesterol by agents such as HMG-CoA reductase inhibitors, for example statins such as simvastatin and fluvastatin, which also by up-regulation of LDL-receptors will promote the cholesterol removal from the plasma; (ii) blocking the bile acid reabsorption by specific agents resulting in increased bile acid excretion and synthesis of bile acids from cholesterol with agents such as bile acid binders, such as resins e.g. cholestyramine and cholestipol; and (iii) by blocking the intestinal uptake of cholesterol by selective cholesterol absorption inhibitors. High density lipoprotein (HDL) elevating agents such as fibrates and nicotinic acid analogues have also been employed.

Even with the current diverse range of therapeutic agents, a significant proportion of the hypercholesterolaemic population is unable to reach target cholesterol levels, or drug interactions or drug safety preclude the long term use needed to reach the target levels. Therefore there is still a need to develop additional agents that are more efficacious and are better tolerated.

Compounds possessing such cholesterol absorption inhibitory activity have been described, see for instance the compounds described in WO 93/02048, WO 94/17038, WO 95/08532, WO 95/26334, WO 95/35277, WO 96/16037, WO 96/19450, WO 97/16455, WO 02/50027, WO 02/50060, WO 02/50068, WO 02/50090, WO 02/66464, WO 04/000803, WO 04/000804, WO04/000805, U.S. Pat. No. 5,756,470, U.S. Pat. No. 5,767,115 and U.S. RE37721.

The present invention is based on the discovery that certain 2-azetidinone derivatives surprisingly inhibit cholesterol absorption. Such properties are expected to be of value in the treatment of disease states associated with hyperlipidaemic conditions. The compounds of the present invention are not disclosed in any of the above applications and we have surprisingly found that the compounds of the present invention possess beneficial efficacious, metabolic and toxicological profiles that make them particularly suitable for in vivo administration to a warm blooded animal, such as man. In particular certain compounds of the present invention have a low degree of absorption compared to compounds of the prior art whilst retaining their ability to inhibit cholesterol absorption.

Accordingly there is provided a single diastereomeric compound of formula (I):

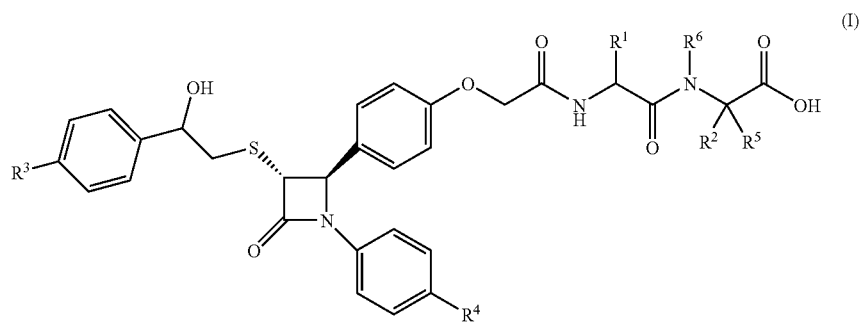

wherein:

$R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, N—$(C_{1-6}$alkyl)amino, N,N—$(C_{1-6}$alkyl)$_2$amino, $C_1$-$C_6$ alkylcarbonylamino $C_{1-6}$alkylS(O)$_a$ wherein a is 0-2, $C_{3-6}$cycloalkyl or aryl; and wherein any aryl group may be optionally substituted by one or two substituents selected from halo, hydroxy, $C_{1-6}$alkyl or $C_{1-6}$alkoxy;

$R^2$ is hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, $(C_1$-$C_4$ alkyl)$_3$Si, N—$(C_{1-6}$alkyl)amino, N,N—$(C_{1-6}$alkyl)$_2$amino, $C_{1-6}$alkylS(O)$_a$ wherein a is 0-2, $C_{3-6}$cycloalkyl or aryl; and wherein any aryl group may be optionally substituted by one or two substituents selected from halo, hydroxy, $C_{1-6}$alkyl or $C_{1-6}$alkoxy;

$R^3$ is hydrogen, alkyl, halo or $C_{1-6}$alkoxy;

$R^4$ is hydrogen, halo or $C_{1-6}$alkoxy;

$R^5$ is hydrogen, $C_{1-6}$ alkyl, arylalkyl, or aryl$C_{1-6}$ alkyl;

$R^6$ is hydrogen, $C_{1-6}$ alkyl, or aryl$C_{1-6}$alkyl;

wherein $R^5$ and $R^2$ may form a ring with 2-7 carbon atoms and wherein $R^6$ and $R^2$ may form a ring with 3-6 carbon atoms;

or a pharmaceutically acceptable salt, solvate, solvate of such a salt or a prodrug thereof.

In one aspect of the invention $R^1$ is hydrogen. According to another aspect of the invention, $R^2$ is hydrogen, a branched or unbranched $C_{1-6}$alkyl, $C_{3-6}$cycloalkyl or aryl; wherein said $C_{1-6}$alkyl may be optionally substituted by one or more hydroxy, amino, $C_{1-6}$alkylS(O)$_a$ wherein a is 0-2, $C_{3-6}$cycloalkyl or aryl; and wherein any aryl group may be optionally substituted by hydroxy. According to a further aspect of the invention, $R^3$ is hydrogen, methoxy, or an alkyl, for instance methyl, or a halogen, for instance chlorine or fluorine. According to yet another aspect of the invention $R^4$ is halo, chlorine or fluorine. According to a further aspect of the invention, $R^6$ is hydrogen, aryl$C_{1-6}$ or $R^6$ and $R^2$ form a ring with 3-6 carbon atoms.

According to one aspect of the invention $R^1$ is hydrogen, $R^2$ is a branched or unbranched $C_{1-4}$alkyl, optionally substituted by a $C_{3-6}$cycloalkyl or an amino, $R^3$ and $R^4$ are halo, $R^5$ is hydrogen or $C_{1-6}$ alkyl, and $R^6$ is hydrogen.

The invention further provides for one or more compounds chosen from:

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-D-valine;

1-[(N-{[4-((2R,3R)-1-(4-chlorophenyl)-3-{[(2R or S)-2-(4-chlorophenyl)-2-hydroxyethyl]thio-}4-oxoazetidin-2-yl)phenoxy]acetyl}glycyl)amino]cyclopropanecarboxylic acid;

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-3-methyl-D-valine;

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-3-cyclohexyl-D-alanine;

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-β,β-dimethyl-D-phenylalanine;

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-D-lysine.

According to an embodiment of the invention it is provided for one or more compounds chosen from:

N-{[4-((2R,3R)-1-(4-fluorophenyl)-3-{[(2R)-2-(4-fluorophenyl)-2-hydroxyethyl]thio}-4-oxoazetidin-2-yl)phenoxy]acetyl}glycyl-D-valine;

1-[(N-{[4-((2R,3R)-1-(4-chlorophenyl)-3-{[(2R)-2-(4-chlorophenyl)-2-hydroxyethyl]thio}-4-oxoazetidin-2-yl)phenoxy]acetyl}glycyl)amino]cyclopropanecarboxylic acid;

N-{[4-((2R,3R)-1-(4-fluorophenyl)-3-{[(2R)-2-(4-fluorophenyl)-2-hydroxyethyl]thio}-4-oxoazetidin-2-yl)phenoxy]acetyl}glycyl-3-methyl-D-valine;

N-{[4-((2R,3R)-1-(4-fluorophenyl)-3-{[(2R)-2-(4-fluorophenyl)-2-hydroxyethyl]thio}-4-oxoazetidin-2-yl)phenoxy]acetyl}glycyl-3-cyclohexyl-D-alanine;

N-{[4-((2R,3R)-1-(4-fluorophenyl)-3-{[(2R)-2-(4-fluorophenyl)-2-hydroxyethyl]thio}-4-oxoazetidin-2-yl)phenoxy]acetyl}glycyl-β,β-dimethyl-D-phenylalanine;

N-{[4-((2R,3R)-1-(4-fluorophenyl)-3-{[(2R)-2-(4-fluorophenyl)-2-hydroxyethyl]thio}-4-oxoazetidin-2-yl)phenoxy]acetyl}glycyl-D-lysine.

According to an embodiment of the invention it is provided for one or more compounds chosen from:

N-{[4-((2R,3R)-1-(4-fluorophenyl)-3-{[(2S)-2-(4-fluorophenyl)-2-hydroxyethyl]thio}-4-oxoazetidin-2-yl)phenoxy]acetyl}glycyl-D-valine;

1-[(N-{[4-((2R,3R)-1-(4-chlorophenyl)-3-{[(2S)-2-(4-chlorophenyl)-2-hydroxyethyl]thio}-4-oxoazetidin-2-yl)phenoxy]acetyl}glycyl)amino]cyclopropanecarboxylic acid;

N-{[4-((2R,3R)-1-(4-fluorophenyl)-3-{[(2S)-2-(4-fluorophenyl)-2-hydroxyethyl]thio}-4-oxoazetidin-2-yl)phenoxy]acetyl}glycyl-3-methyl-D-valine;

N-{[4-((2R,3R)-1-(4-fluorophenyl)-3-{[(2S)-2-(4-fluorophenyl)-2-hydroxyethyl]thio}-4-oxoazetidin-2-yl)phenoxy]acetyl}glycyl-3-cyclohexyl-D-alanine;

N-{[4-((2R,3R)-1-(4-fluorophenyl)-3-{[(2S)-2-(4-fluorophenyl)-2-hydroxyethyl]thio}-4-oxoazetidin-2-yl)phenoxy]acetyl}glycyl-β,β-dimethyl-D-phenylalanine;

N-{[4-((2R,3R)-1-(4-fluorophenyl)-3-{[(2S)-2-(4-fluorophenyl)-2-hydroxyethyl]thio}-4-oxoazetidin-2-yl)phenoxy]acetyl}glycyl-D-lysine.

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" would include benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

The term "aryl" refers to a 4-10 membered aromatic mono or bicyclic ring containing 0 to 5 heteroatoms independently selected from nitrogen, oxygen or sulphur. Examples of aryls include phenyl, pyrrolyl, furanyl, imidazolyl, triazolyl, tetrazolyl, pyrazinyl, pyrimidinyl, pyridazinyl, pyridyl, isoxazolyl, oxazolyl, 1,2,4 oxadiazolyl, isothiazolyl, thiazolyl, 1,2,4-triazolyl, thienyl, naphthyl, benzofuranyl, benzimidazolyl, benzthienyl, benzthiazolyl, benzisothiazolyl, benzoxazolyl, benzisoxazolyl, 1,3-benzodioxolyl, indolyl, pyridoimidazolyl, pyrimidoimidazolyl, quinolyl, isoquinolyl, quinoxalinyl, quinazolinyl, phthalazinyl, cinnolinyl and naphthyridinyl. Particularly "aryl" refers to phenyl, thienyl, pyridyl, imidazolyl or indolyl.

Examples of "$C_{1-6}$alkoxy" include methoxy, ethoxy and propoxy. Examples of "$C_{1-6}$alkylS(O)$_a$ wherein a is 0 to 2" include methylthio, ethylthio, methylsulphinyl, ethylsulphinyl, mesyl and ethylsulphonyl. Examples of "N—($C_{1-6}$alkyl) amino" include methylamino and ethylamino. Examples of "N,N—($C_{1-6}$alkyl)$_2$amino" include di-N-methylamino, di-(N-ethyl)amino and N-ethyl-N-methylamino. "$C_{3-6}$cycloalkyl" refers to cyclopropyl, cyclobutyl, cyclopentyl and cyclohexyl.

A suitable pharmaceutically acceptable salt of a compound of the invention, or other compounds disclosed herein, is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetate or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I), or other compounds disclosed herein, may be administered in the form of a prodrug which is broken down in the human or animal body to give a compound of the formula (I). examples of pro-drugs include in vivo hydrolysable esters and in vivo hydrolysable amides of a compound of the formula (I).

An in vivo hydrolysable ester of a compound of the formula (I), or other compounds disclosed herein, containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I), or other compounds disclosed herein, containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethyl-propionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I), or other compounds disclosed herein, containing a carboxy group is, for example, a N—$C_{1-6}$ alkyl or N,N-di-$C_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess cholesterol absorption inhibitory activity.

The invention relates to any and all tautomeric forms of the compounds of the formula (I) that possess cholesterol absorption inhibitory activity.

It is also to be understood that certain compounds of the formula (I) can exist in solvated as well as unsolvated forms such as, for example, hydrated forms. It is to be understood that the invention encompasses all such solvated forms which possess cholesterol absorption inhibitory activity.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I)) comprises of:

Process 1) Reacting a Compound of Formula (II):

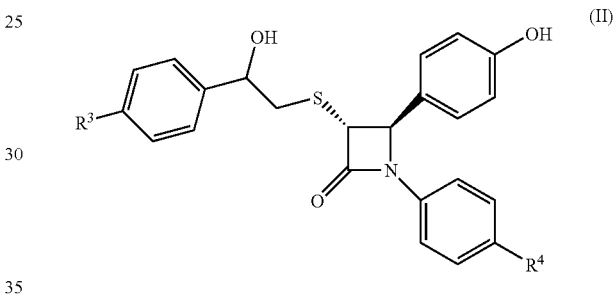

with a compound of formula (III):

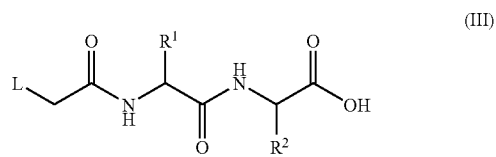

wherein L is a displaceable group;

Process 2) Reacting an Acid of Formula (IV):

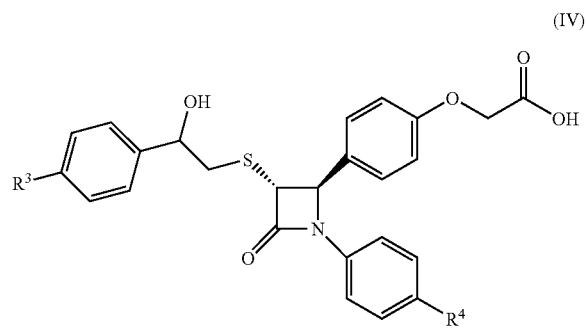

or an activated derivative thereof; with an amine of formula (V):
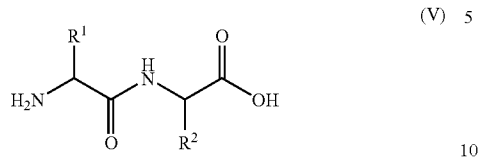
(V)
Process 3): Reacting an Acid of Formula (VI):
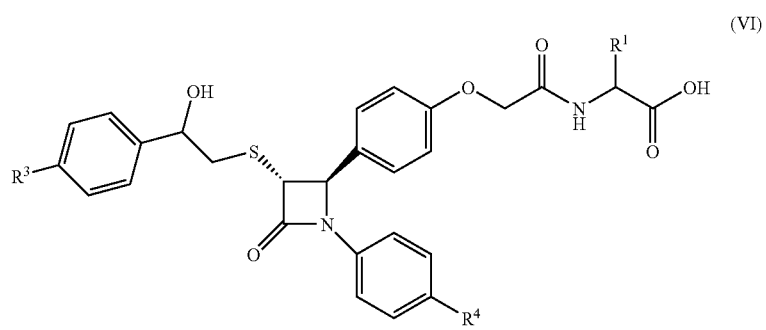
(VI)
or an activated derivative thereof, with an amine of formula (VII):
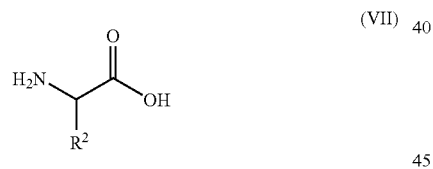
(VII)
Process 4): Reducing a Compound of Formula (VIII):
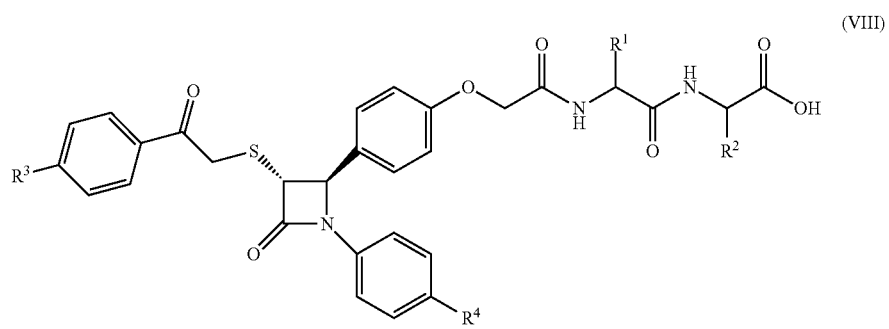
(VIII)

Process 5): Reacting a Compound of Formula (IX):

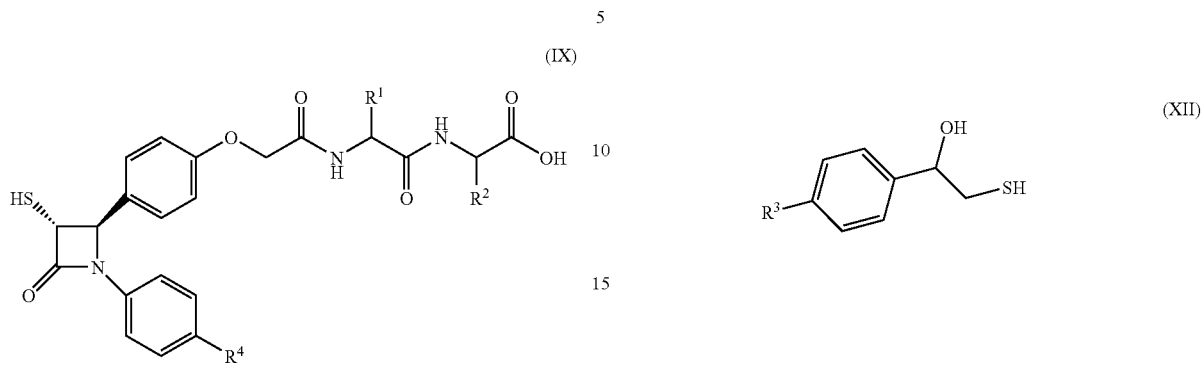

with a compound of formula (X):

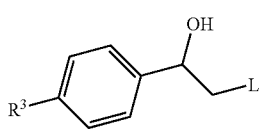

wherein L is a displaceable group;

Process 6): Reacting a Compound of Formula (XI):

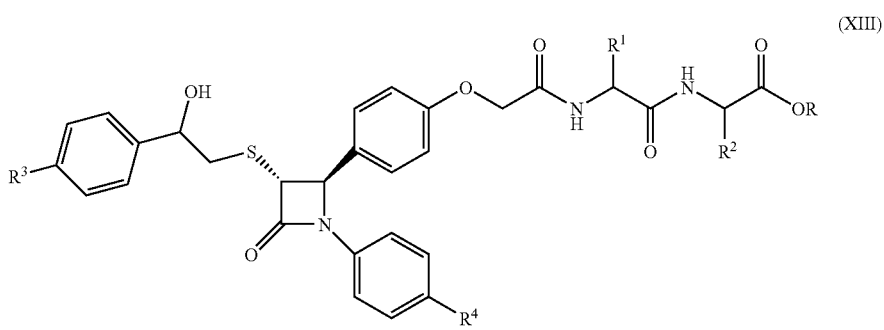

wherein L is a displaceable group; with a compound of formula (XII):

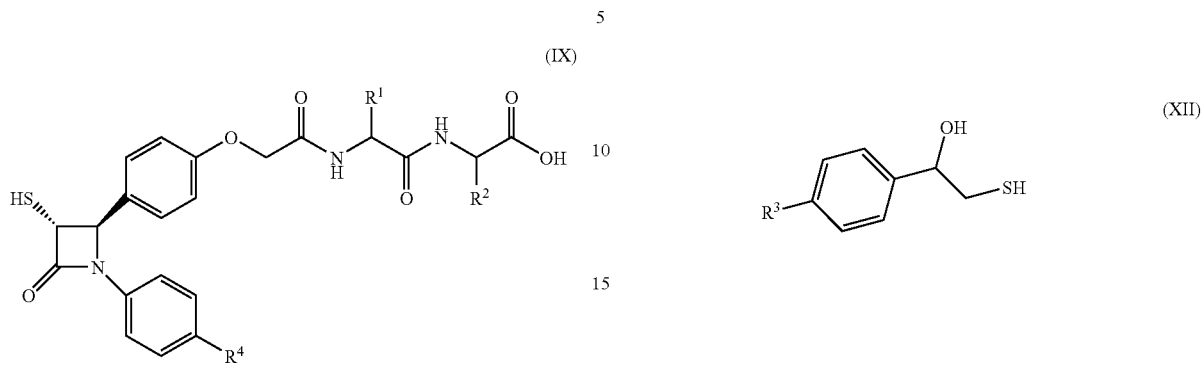

Process 7): De-Esterifying a Compound of Formula (XIII)

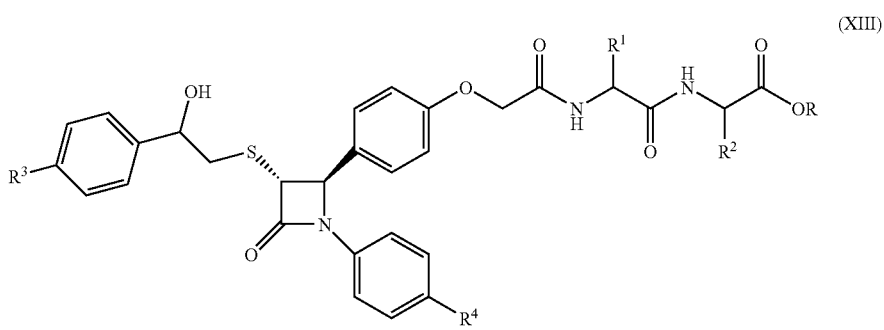

wherein the group C(O)OR is an ester group;

and thereafter if necessary or desirable:

i) converting a compound of the formula (I) into another compound of the formula (I);

ii) removing any protecting groups;

iii) forming a pharmaceutically acceptable salt, solvate, solvate of such a salt or a prodrug; or iv) separating two or more enantiomers.

L is a displaceable group, suitable values for L are for example, a halogeno or sulphonyloxy group, for example a chloro, bromo, methanesulphonyloxy or toluene-4-sulphonyloxy group.

C(O)OR is an ester group, suitable values for C(O)OR are methoxycarbonyl, ethoxycarbonyl, t-butoxycarbonyl and benzyloxycarbonyl.

The starting materials used in the present invention can be prepared by modifications of the routes described in EP 0 792 264 B1. Alternatively they can be prepared by the following reactions.

Process 1): Alcohols of formula (II) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (II) may be prepared according to the following scheme:
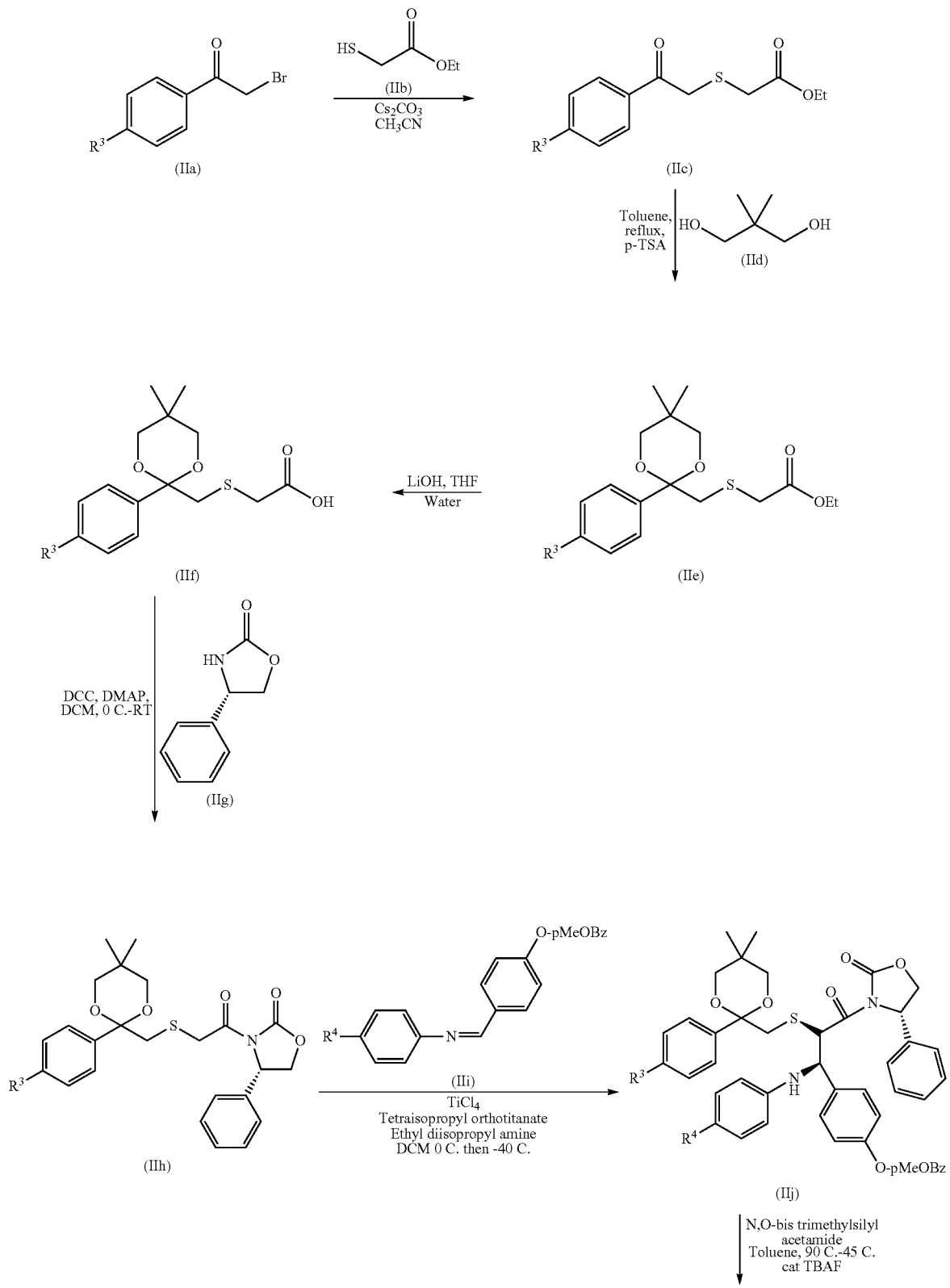

-continued

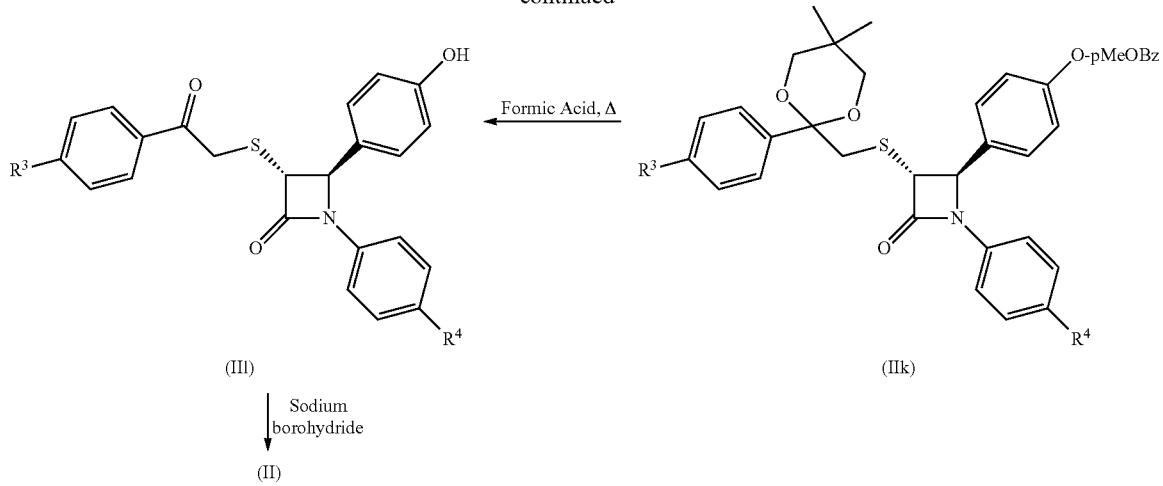

(III) ← Formic Acid, Δ ← (IIk)

| Sodium borohydride (II)

wherein pMeOBz is para methoxy benzyl.

Compounds of formula (IIb), (IId), (IIg) and (III) are commercially available compounds, or they are known in the literature, or they are prepared by standard processes known in the art.

A compound of formula (III) may also be reacted with a compound of formula (XIV).

Compounds of formula (XIV) may be prepared according to the following route:

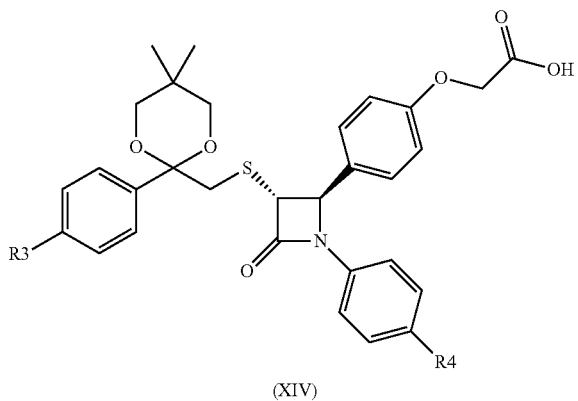

(XIV)

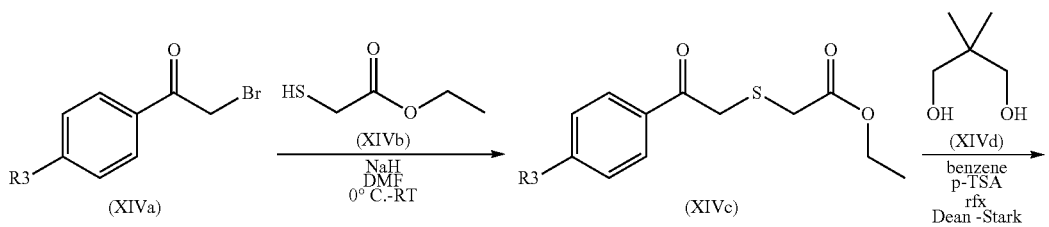

-continued
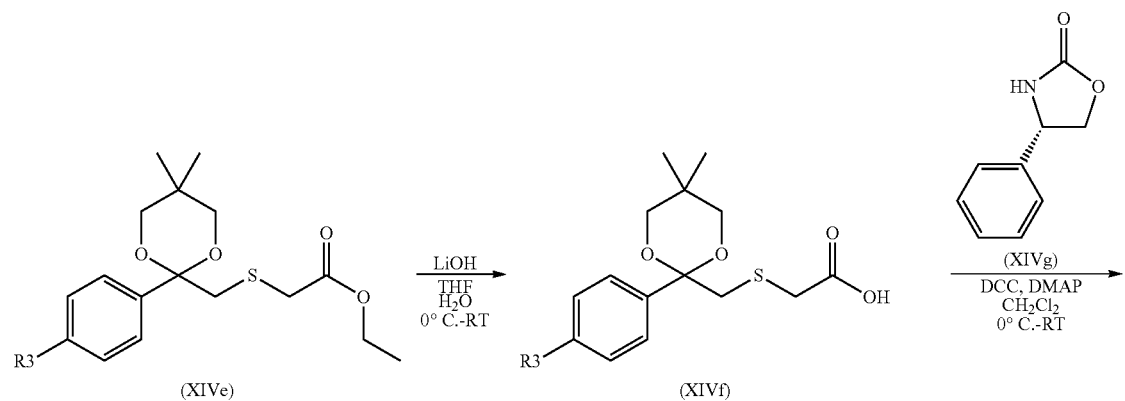
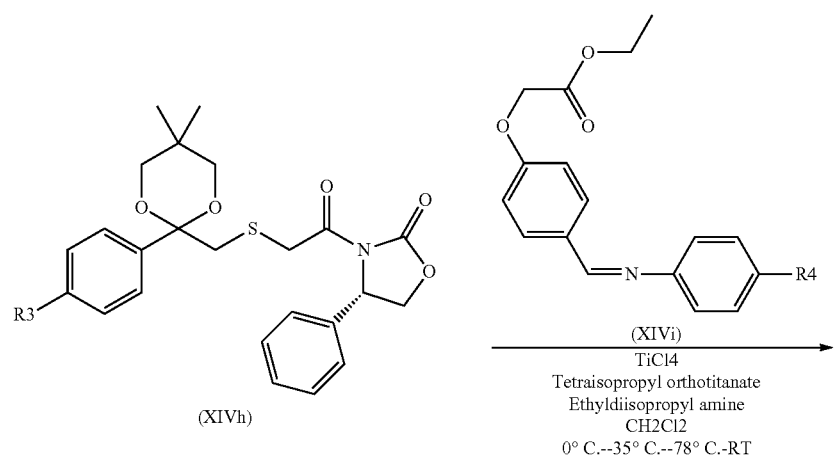
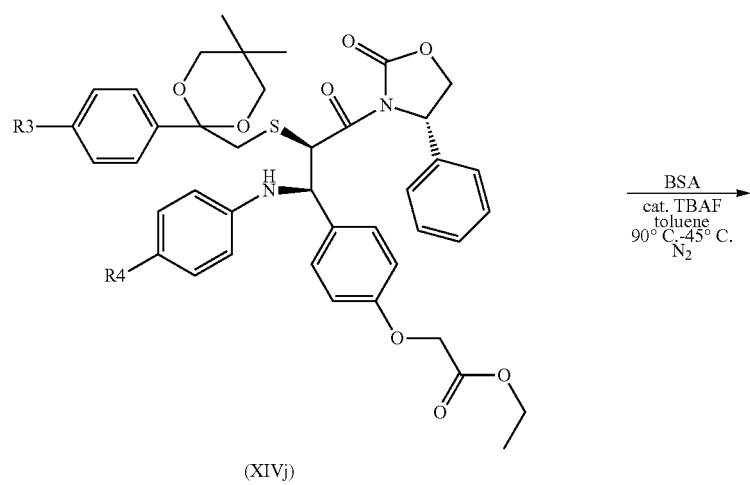

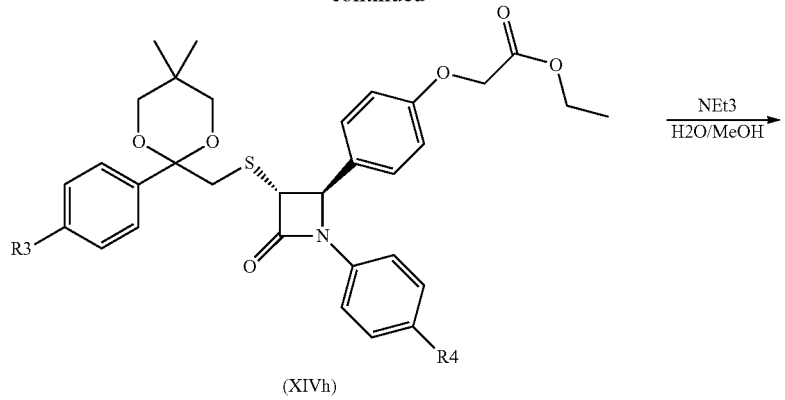

(XIVh)

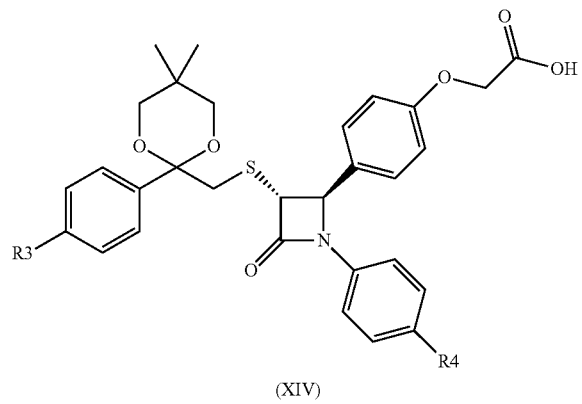

(XIV)

Compounds of formula XIVi may be prepared by the following route:

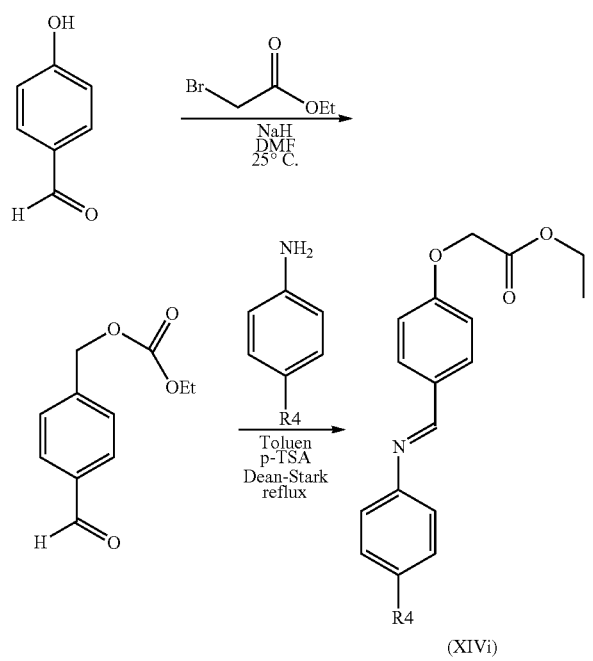

(XIVi)

Process 2) and Process 3): Acids and amines may be coupled together in the presence of a suitable coupling reagent. Standard peptide coupling reagents known in the art can be employed as suitable coupling reagents, for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Acids of formula (IV) and (VI) may be prepared from compounds of formula (II) by reacting them with the appropriate, optionally protected, side chain using the conditions of Process 1). Alternatively, acids of formula (IV) and (VI) may be prepared by a modification of Scheme I.

Amines of formula (V) and (VII) are commercially available compounds, or they are known in the literature, or they are prepared by standard processes known in the art.

Process 4): Reduction of compounds of formula (VIII) could be performed with a hydride reagent such as sodium borohydride in a solvent such as methanol at temperatures suitable between −20-40° C.

Compounds of formula (VIII) can be prepared from compounds of formula (III), by deprotecting the benzyl group and performing Process 1. Alternatively compound (IIk) could be debenzylated, Process 1 could be performed and the resulting compound deprotected to reveal the ketone.

Process 5) and Process 6): these compounds may be reacted together in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (IX) and (XI) may be prepared by an appropriate modification of Scheme 1.

Compounds of formula (X) and (XII) are commercially available compounds, or they are known in the literature, or they are prepared by standard processes known in the art.

Process 7): Esters of formula (XIII) may be deprotected under standard conditions such as those described below, for example a methyl or ethyl ester may be deprotected with sodium hydroxide in methanol at room temperature.

Compounds of formula (XIII) may be prepared by a modification of any of the processes described herein for the preparation of compounds of formula (I).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1999). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess cholesterol absorption inhibitory activity. These properties may be assessed, using the following biological tests.

In Vivo Testing of Cholesterol Absorption Inhibitors (A)

C57BL/6 female mice were maintained on regular chow diet and housed in individual cages to collect faeces. Mice were fasted for 3 hours and then gavaged with vehicle or compound. Half an hour later the mice were gavaged with radiolabelled cholesterol. Six hours after the $^{14}$C-cholesterol gavage blood samples were taken via the tail and plasma prepared to determine how much cholesterol were absorbed. 24 hours after the gavage of $^{14}$C-cholesterol the mice were bled and plasma were prepared for analysis. Faeces were collected for 24 hours to assess absorption efficiency.

In Vivo Testing of Cholesterol Absorption Inhibitors (B).

C57BL/6 female mice were maintained on regular chow diet and housed in individual cages to collect faeces. Mice were fasted for 3 hours and then gavaged with vehicle or compound. One to ten hours later the mice were gavaged with radiolabelled cholesterol. Six hours after the $^{14}$C-cholesterol gavage blood sample was taken via the tail and plasma prepared to determine how much cholesterol was absorbed. 24 hours after the gavage of $^{14}$C-cholesterol the mice were bled and plasma analysed for radioactivity. Faeces were also collected for 24 hours to assess absorption efficiency.

REFERENCES

1. E. A. Kirk, G. L. Moe, M. T. Caldwell, J. Å. Lernmark, D. L. Wilson, R. C. LeBoeuf. Hyper- and hypo-responsiveness to dietary fat and cholesterol among inbred mice: searching for level and variability genes. J. Lipid Res. 1995 36:1522-1532.
2. C. P. Carter, P. N. Howles, D. Y. Hui. Genetic variation in cholesterol absorption efficiency among inbred strains of mice. J. Nutr. 1997 127:1344-1348.
3. C. D. Jolley, J. M. Dietschy, S. D. Turley. Genetic differences in cholesterol absorption in 129/Sv and C57BL/6 mice: effect on cholesterol responsiveness. Am. J. Physiol. 1999 276:G1117-G1124.

Administration of 0.2 µmol/kg of Example 3 gave 73% inhibition of $^{14}$C-cholesterol absorption (procedure A). Administration of 0.2 µmol/kg of Example 4 gave 75% inhibition of $^{14}$C-cholesterol absorption (procedure A) and administration of 0.2 µmol/kg of Example 5 gave 78% inhibition of $^{14}$C-cholesterol absorption (procedure A).

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range of approximately 0.02-100 mg/kg, preferably 0.02-50 mg/kg, and this normally provides a therapeutically-effective dose. A unit dose form such as a tablet or capsule will usually contain, for example 1-250 mg of active ingredient. Preferably a daily dose in the range of 1-50 mg/kg, particularly 0.1-10 mg/kg is employed. In another aspect a daily dose in the rage of 0.01-20 mg/kg is employed. In one aspect of the invention the daily dose of a compound of formula (I) is less than or equal to 100 mg. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective cholesterol absorption inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of a cholesterol absorption inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the production of a cholesterol absorption inhibitory effect in a warm-blooded animal, such as man.

Herein, where the production of a cholesterol absorption inhibitory effect or a cholesterol lowering effect is stated, suitably this relates to the treatment of hyperlipidaemic conditions in a warm-blooded animal, such as man. Additionally is relates to the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man. Furthermore it relates to the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in a warm-blooded animal, such as man. It also relates to the treatment of atherosclerosis, coronary heart diseases, myocardial infarction, angina pectoris, peripheral vascular diseases, stroke and transient ischaemic attacks in a warm-blooded animal, such as man.

The production of a cholesterol absorption inhibitory effect or a cholesterol lowering effect also relates to a method of treating and/or preventing atherosclerotic lesions, a method of preventing plaque rupture and a method of promoting lesion regression. Furthermore it relates to a method of inhibiting monocytes-macrophage accumulation in atherosclerotic lesions, a method of inhibiting expression of matrix metalloproteinases in atherosclerotic lesions, a method of inhibiting the destabilization of atherosclerotic lesions, a method for preventing atherosclerotic plaque rupture and a method of treating unstable angina.

The production of a cholesterol absorption inhibitory effect or a cholesterol lowering effect also relates to a method of treating sitosterolemia.

Compounds of formula (I), or a pharmaceutically acceptable salt, solvate, solvate of such a salt or a prodrug thereof may also have value in the treatment or prevention of Alzeheimer's Disease (see for example WO 02/096415). Therefore in a further aspect of the invention, there is provided a compound of formula (I), or a pharmaceutically acceptable salt, solvate, solvate of such a salt or a prodrug thereof, for use in the treatment or prevention of Alzheimer's Disease.

Compounds of formula (I), or a pharmaceutically acceptable salt, solvate, solvate of such a salt or a prodrug thereof may also have value in the treatment or prevention of vascular inflammation (see for example WO 03/026644). Therefore in a further aspect of the invention, there is provided a compound of formula (I), or a pharmaceutically acceptable salt, solvate, solvate of such a salt or a prodrug thereof, for use in the treatment or prevention of vascular inflammation.

According to a further feature of this aspect of the invention there is provided a method for producing a cholesterol absorption inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

The cholesterol absorption inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional cholesterol absorption inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with cholesterol biosynthesis inhibitors, or pharmaceutically acceptable salts, solvates, solvates of such salts or prodrugs thereof. Suitable cholesterol biosynthesis inhibitors include HMG Co-A reductase inhibitors, squalene synthesis inhibitors and squalene epoxidase inhibitors. A suitable squalene synthesis inhibitor is squalestatin 1 and a suitable squalene epoxidase inhibitor is NB-598.

In this aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and rosuvastatin, or a pharmaceutically acceptable salt, solvate, solvate of such a salt or a prodrug thereof. A further particular statin is pitvastatin, or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is rosuvastatin, or a pharmaceutically acceptable salt, solvate, solvate of such a salt or a prodrug thereof. A preferable particular statin is rosuvastatin calcium salt.

Therefore in an additional feature of the invention, there is provided a combination of a compound of formula (I), or a pharmaceutically acceptable salt, solvate, solvate of such a salt or a prodrug thereof and an HMG Co-A reductase inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;

b) an HMG Co-A reductase inhibitor, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) an HMG Co-A reductase inhibitor, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of a cholesterol lowering effect.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a A further suitable compound possessing IBAT inhibitory activity for use in combination with compounds of the present invention is S-8921 (EP 597 107).

A further suitable IBAT inhibitor for use in combination with compounds of the present invention is the compound:

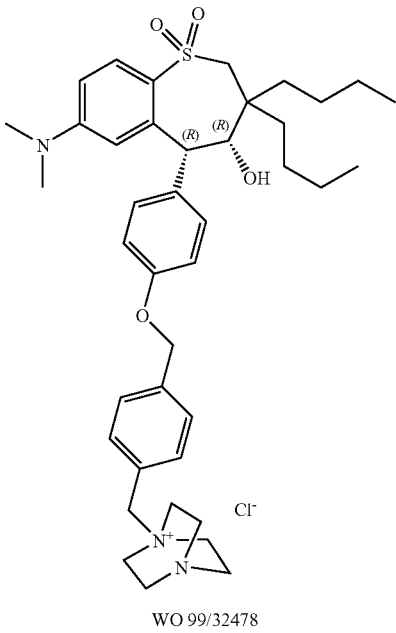

WO 99/32478

A particular IBAT inhibitor for use in combination with compounds of the present invention is selected from any one of Examples 1-120 of WO 02/50051, or a pharmaceutically acceptable salt, solvate, solvate of such a salt or a prodrug thereof, and the compounds of Examples 1-120 are incorporated herein by reference. Claims 1-15 of WO 02/50051 are also incorporated herein by reference. A particular IBAT inhibitor selected from WO 02/50051 for use in combination with compounds of the present invention is selected from any one of:

1,1-dioxo-3,3-dibutyl-5-phenyl-7-methylthio-8-(N-{(R)-1'-phenyl-1'-[N'-(carboxymethyl) carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine; prodrug thereof, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of a matrix metalloproteinase inhibitor.

In another aspect of the invention, the compound of formula (I), or a pharmaceutically acceptable salt, solvate, solvate of such a salt or a prodrug thereof, may be administered in association with an ileal bile acid (IBAT) inhibitor or a pharmaceutically acceptable salt, solvate, solvate of such a salt or a prodrug thereof. Suitable compounds possessing IBAT inhibitory activity for use in combination with compounds of the present invention have been described, see for instance the compounds described in WO 93/16055, WO 94/18183, WO 94/18184, WO 94/24087, WO 96/05188, WO 96/08484, WO 96/16051, WO 97/33882, WO 98/07749, WO 98/38182, WO 98/40375, WO 98/56757, WO 99/32478, WO 99/35135, WO 99/64409, WO 99/64410, WO 00/01687, WO 00/20392, WO 00/20393, WO 00/20410, WO 00/20437, WO 00/35889, WO 01/34570, WO 00/38725, WO 00/38726, WO 00/38727, WO 00/38728, WO 00/38729, WO 00/47568, WO 00/61568, WO 01/66533, WO 01/68096, WO 01/68637, WO 02/08211, DE 19825804, JP 10072371, U.S. Pat. No. 5,070,103, EP 251 315, EP 417 725, EP 489 423, EP 549 967, EP 573 848, EP 624 593, EP 624 594, EP 624 595, EP 864 582, EP 869 121 and EP 1 070 703 and the contents of these patent applications are incorporated herein by reference. Particularly the named examples of these patent applications are incorporated herein by reference. More particularly claim 1 of these patent application are incorporated herein by reference.

Other suitable classes of IBAT inhibitors for use in combination with compounds of the present invention are the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity for use in combination with compounds of the present invention is (3R,5R)-3-butyl-3-ethyl-1,1-dioxido-5-phenyl-2,3,4,5-tetrahydro-1,4-benzothiazepin-8-yl □-D-glucopyranosiduronic acid (EP 864 582).

1,1-dioxo-3-butyl-3-ethyl-5-phenyl-7-methylthio-8-(N-{(R)-α-[N'-(2-sulphoethyl) carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'—(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—(R)-(2-hydroxy-1-carboxyethyl)carbamoyl]benzyl}carbamoyl-methoxy)-2,3,4,5-tetrahydro-1,5-benzothiazepine;

1,1-dioxo-3,3-dibutyl-5-phenyl-7-methylthio-8-{N—[(R)-α-(N'-{(R)-1-[N''-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphoryl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-{N—[(R)-α-(N'-{2-[(hydroxy)(methyl)phosphoryl]ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N—[(R)-α-(N'-{2-[(methyl)(ethyl) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N—[(R)-α-(N'-{2-[(methyl)(hydroxy)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)—N'-(2-methylsulphinyl-1-carboxyethyl)carbamoyl]benzyl}carbamoylmethoxy)-2,3,4,5-tetrahydro-1,5-benzothiazepine; and 1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;

or a pharmaceutically acceptable salt, solvate, solvate of such a salt or a prodrug thereof.

A particular IBAT inhibitor for use in combination with compounds of the present invention is selected from any one of Examples 1-44 of WO 03/020710, or a pharmaceutically acceptable salt, solvate, solvate of such a salt or a prodrug thereof, and the compounds of Examples 1-44 are incorporated herein by reference. Claims 1-10 of WO 03/020710 are also incorporated herein by reference. A particular IBAT inhibitor selected from WO 03/020710 for use in combination with compounds of the present invention is selected from any one of:

1,1-dioxo-3,3-dibutyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'—((S)-1-carbamoyl-2-hydroxyethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(hydroxycarbamoyl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N—((R)-α-{N'-[2-(N'-pyrimidin-2-ylureido)ethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-[N—((R)-α-{N'-[2-(N'-pyridin-2-ylureido)ethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-(N-{(R)-α-[N-(1-t-butoxycarbonylpiperidin-4-ylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2,3-dihydroxypropyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N—((R)-α-{N'-[2-(3,4-dihydroxyphenyl)-2-methoxyethyl]carbamoyl}benzyl)carbamoylmethoxy]-2,3,4,5-tetrahydro-1,5-benzothiazepine 1,1-dioxo-3-butyl-3-ethyl-5-phenyl-7-methylthio-8-(N-{(R)-α-[N'-(2-aminoethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(piperidin-4-ylmethyl) carbamoyl]benzyl}carbamoylmethoxy)-2,3,4,5-tetrahydro-1,5-benzothiazepine; or 1,1-dioxo-3-butyl-3-ethyl-5-phenyl-7-methylthio-8-(N-{(R)-α-[N'-(2-N,N-dimethylaminosulphamoylethyl)carbamoyl]benzyl}carbamoylmethoxy)-2,3,4,5-tetrahydro-1,5-benzothiazepine;

or a pharmaceutically acceptable salt, solvate, solvate of such a salt or a prodrug thereof.

A particular IBAT inhibitor for use in combination with compounds of the present invention is selected from any one of Examples 1-7 of WO 03/022825, or a pharmaceutically acceptable salt, solvate, solvate of such a salt or a prodrug thereof, and the compounds of Examples 1-7 are incorporated herein by reference. Claims 1-8 of WO 03/022825 are also incorporated herein by reference. A particular IBAT inhibitor selected from WO 03/022825 for use in combination with compounds of the present invention is selected from any one of:

1,1-dioxo-3(R)-3-butyl-3-ethyl-5-(R)-5-phenyl-8-[N—((R)-α-carboxybenzyl)carbamoylmethoxy]-2,3,4,5-tetrahydro-1,4-benzothiazepine;

1,1-dioxo-3(S)-3-butyl-3-ethyl-5-(S)-5-phenyl-8-[N—((R)-α-carboxybenzyl)carbamoylmethoxy]-2,3,4,5-tetrahydro-1,4-benzothiazepine;

1,1-dioxo-3(R)-3-butyl-3-ethyl-5-(R)-5-phenyl-8-(N-{(R)-α-[N-(carboxymethyl)carbamoyl]benzyl}carbamoylmethoxy)-2,3,4,5-tetrahydro-1,4-benzothiazepine;

1,1-dioxo-3(S)-3-butyl-3-ethyl-5-(S)-5-phenyl-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-bromo-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-(S)-3-ethyl-3-butyl-4-hydroxy-5-(S)-5-phenyl-7-bromo-8-(N-{(R)-α-[N-(carboxymethyl)carbamoyl]benzyl}carbamoylmethoxy)-2,3,4,5-tetrahydro-1,4-benzothiazepine 3,5-trans-1,1-dioxo-3-(R)-3-ethyl-3-butyl-4-hydroxy-5-(R)-5-phenyl-7-bromo-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,4-benzothiazepine ammonia salt;

1,1-dioxo-3-(S)-3-ethyl-3-butyl-5-(S)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt; and 1,1-dioxo-3-(R)-3-ethyl-3-butyl-5-(R)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt;

or a pharmaceutically acceptable salt, solvate, solvate of such a salt or a prodrug thereof.

A particular IBAT inhibitor for use in combination with compounds of the present invention is selected from any one of Examples 1-4 of WO 03/022830, or a pharmaceutically acceptable salt, solvate, solvate of such a salt or a prodrug thereof, and the compounds of Examples 14 are incorporated herein by reference. Claims 1-8 of WO 03/022830 are also incorporated herein by reference. A particular IBAT inhibitor selected from WO 03/022830 for use in combination with compounds of the present invention is selected from any one of:

1,1-dioxo-3-butyl-3-ethyl-4-hydroxy-5-phenyl-7-(N-{(R)-α-[N-(carboxymethyl)carbamoyl]benzyl}carbamoylmethylthio)-2,3,4,5-tetrahydrobenzothiepine 1,1-dioxo-3-butyl-3-ethyl-4-hydroxy-5-phenyl-7-(N-{(R)-α-[N-(2-sulphoethyl)carbamoyl]-4-hydroxybenzyl}carbamoylmethylthio)-2,3,4,5-tetrahydrobenzothiepine ammonia salt 1,1-dioxo-3-butyl-3-ethyl-4-hydroxy-5-phenyl-7-{N-[α-(carboxy)-2-fluorobenzyl]carbamoylmethylthio}-2,3,4,5-tetrahydrobenzothiepine; and 1,1-dioxo-3-butyl-3-ethyl-4-hydroxy-5-phenyl-7-{N-[1-(carboxy)-1-(thien-2-yl)methyl]carbamoylmethylthio}-2,3,4,5-tetrahydrobenzothiepine or a pharmaceutically acceptable salt, solvate, solvate of such a salt or a prodrug thereof.

A particular IBAT inhibitor for use in combination with compounds of the present invention is selected from any one of Examples 1-39 of WO 03/022286, or a pharmaceutically acceptable salt, solvate, solvate of such a salt or a prodrug thereof, and the compounds of Examples 1-39 are incorporated herein by reference. Claims 1-10 of WO 03/022286 are also incorporated herein by reference. A particular IBAT inhibitor selected from WO 03/022286 for use in combination with compounds of the present invention is selected from any one of:

1,1-dioxo-3,3-dibutyl-5-phenyl-7-methylthio-8-(N-{(R)-α-[N—((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxybutyl) carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxypropyl) carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxyethyl)carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxy-2-(R)-hydroxypropyl)carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((R)-1-carboxy-2-methylthioethyl)carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N—((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxy-2-methylpropyl)carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxypropyl) carbamoyl]-4-hydroxybenzyl}carbamoylmethoxy)-2,3,4,5-tetrahydro-1,2,5-benzothiadiazepine; and 1,1-dioxo-3,3-dibutyl-5-phenyl-7-methylthio-8-[N—((R)-α-carboxy-4-hydroxybenzyl)carbamoylmethoxy]-2,3,4,5-tetrahydro-1,2,5-benzothiadiazepine;

or a pharmaceutically acceptable salt, solvate, solvate of such a salt or a prodrug thereof.

A particular IBAT inhibitor for use in combination with compounds of the present invention is selected from any one of Examples 1-7 of WO 03/091232, or a pharmaceutically acceptable salt, solvate, solvate of such a salt or a prodrug thereof, and the compounds of Examples 1-7 are incorporated herein by reference. Claims 1-10 of WO 03/091232 are also incorporated herein by reference. A particular IBAT inhibitor selected from WO 03/091232 for use in combination with compounds of the present invention is selected from any one of:

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N—((R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-{N—[(R)-α-(N-{2-(S)—N-(carbamoylmethyl) carbamoyl]pyrrolidin-1-ylcarbonylmethyl}carbamoyl)benzyl]carbamoylmethoxy}-2,3,4,5-tetrahydro-1,2,5-benzothiadiazepine;

1,1-Dioxo-3,3-dibutyl-5-phenyl-7-methylthio-8-[N—((R)-α-{N-[2-(3,4,5-trihydroxyphenyl)ethyl]carbamoyl}benzyl)carbamoylmethoxy]-2,3,4,5-tetrahydro-1,2,5-benzothiadiazepine; and 1,1-Dioxo-3,3-dibutyl-5-phenyl-7-methylthio-8-(N-{(R)-α-[N-(2-(R)-3-(S)-4-(S)-5-(R)-3,4,5,6-tetrahydroxytetrahydropyran-2-ylmethyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof.

Further suitable compounds possessing IBAT inhibitory activity for use in combination with compounds of the present invention have the following structure of formula (AI):

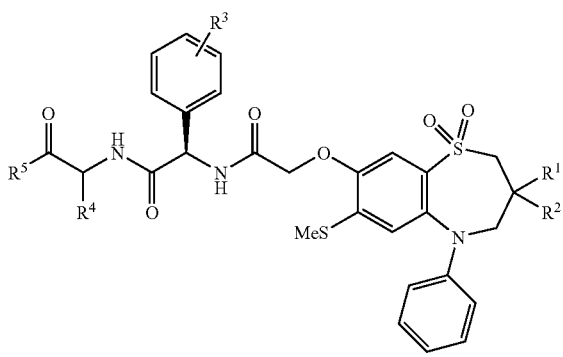

(AI)

wherein:

$R^1$ and $R^2$ are independently selected from $C_{1-4}$alkyl;

$R^3$ is hydrogen, hydroxy or halo;

$R^4$ is $C_{1-4}$alkyl optionally substituted by hydroxy, methoxy and methylS(O)a wherein a is 0-2

$R^5$ is hydroxy or HOC(O)CH($R^6$)NH—;

$R^6$ is selected from hydrogen and $C_{1-3}$alkyl optionally substituted by hydroxy, methoxy and methylS(O)a wherein a is 0-2;

or a pharmaceutically acceptable salt, solvate, solvate of such a salt or a prodrug thereof;

with the proviso that when $R^1$ and $R^2$ are both butyl, $R^5$ is hydroxy and $R^4$ is methylthiomethyl, methylsulphinylmethyl, methylthioethyl, hydroxymethyl, methoxymethyl; $R^3$ is not hydrogen; and with the proviso that when $R^1$ and $R^2$ are both butyl, $R^5$ is HOC(O)CH($R^6$)NH—, $R^6$ is hydroxymethyl and $R^4$ is hydroxymethyl; $R^3$ is not hydrogen.

Suitable IBAT inhibitors having the above structure for use in combination with compounds of the present invention are selected from any one of:

1,1-dioxo-3,3-dibutyl-5-phenyl-7-methylthio-8-(N-{(R)-α-[N'—((S)-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxypropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxybutyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-2-methylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-2-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-3-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-2-hydroxypropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-2-mesylethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-3-methylsulphonylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-3-mesylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxyethyl) carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxypropyl) carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N—((S)-1-carboxybutyl) carbamoyl]-4-hydroxybenzyl}carbamoylmethoxy)-2,3,4,5-tetrahydro-1,5-benzothiazepine;

1,1-dioxo-3,3-dibutyl-5-phenyl-7-methyl thio-8-(N-{(R)-α-[N'—((S)-1-carboxy-2-methylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-2-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-3-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-2-hydroxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-2-hydroxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-2-methylthioethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((8)-1-carboxy-2-methylsulphinylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-2-mesylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-2-methoxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-3-methylthiopropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-3-methylsulphonylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxy-3-mesylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'—((S)-1-carboxypropyl)carbamoyl]-4-hydroxybenzyl}carbamoylmethoxy)-2,3,4,5-tetrahydro-1,5-benzothiazepine; or 1,1-dioxo-3,3-dibutyl-5-phenyl-7-methylthio-8-(N-{(R)-α-[N'—((S)-1-carboxyethyl) carbamoyl] benzyl}carbamoylmethoxy)-2,3,4,5-tetrahydro-1,5-benzothiazepine.

or a pharmaceutically acceptable salt, solvate, solvate of such a salt or a prodrug thereof.

Further suitable IBAT inhibitors for use in combination with compounds of the present invention are those having the structure (BI):

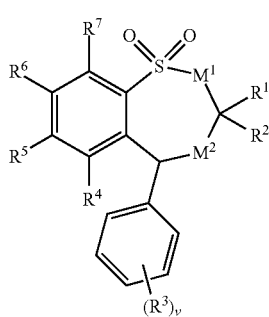

wherein
$M^1$ is —$CH_2$— or —$NR^{21}$—;
$M^2$ is —$CR^{22}R^{23}$— or —$NR^{24}$—; provided that if $M^1$ is —$NR^{21}$—, $M^2$ is —$CR^{22}R^{23}$—;
One of $R^1$ and $R^2$ are selected from hydrogen, $C_{1-6}$alkyl or $C_{2-6}$alkenyl and the other is selected from $C_{1-6}$alkyl or $C_{2-6}$alkenyl;
$R^3$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
v is 0-5;
one of $R^5$ and $R^6$ is a group of formula (BIA):

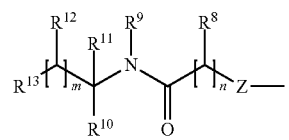

$R^4$ and $R^7$ and the other of $R^5$ and $R^6$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^4$ and $R^7$ and the other of $R^5$ and $R^6$ may be optionally substituted on carbon by one or more $R^{25}$;

Z is —O—, —N($R^a$)—, —S(O)$_b$— or —CH($R^a$)—; wherein $R^a$ is hydrogen or $C_{1-6}$alkyl and b is 0-2;

$R^8$ is hydrogen, $C_{1-4}$alkyl, carbocyclyl or heterocyclyl; wherein $R^8$ may be optionally substituted on carbon by one or more substituents selected from $R^{26}$; and wherein if said heterocyclyl contains an —NH— group, that nitrogen may be optionally substituted by a group selected from $R^{27}$;

$R^9$ is hydrogen or $C_{1-4}$alkyl;

$R^{10}$ and $R^{11}$ are independently selected from hydrogen, $C_{1-4}$alkyl, carbocyclyl or heterocyclyl; or $R^{10}$ and $R^{11}$ together form $C_{2-6}$alkylene; wherein $R^{10}$ and $R^{11}$ or $R^{10}$ and $R^{11}$ together may be independently optionally substituted on carbon by one or more substituents selected from $R^{28}$; and wherein if said heterocyclyl contains an —NH— moiety, that nitrogen may be optionally substituted by one or more $R^{29}$;

$R^{12}$ is hydrogen, $C_{1-4}$alkyl, carbocyclyl or heterocyclyl; wherein $R^{12}$ may be optionally substituted on carbon by one or more substituents selected from $R^{30}$; and wherein if said heterocyclyl contains an —NH— moiety, that nitrogen may be optionally substituted by one or more $R^{31}$;

$R^{13}$ is hydrogen, halo, nitro, cyano, hydroxy, amino, carbamoyl, mercapto, sulphamoyl, hydroxyaminocarbonyl, $C_{1-10}$-alkyl, $C_{2-10}$alkenyl, $C_{2-10}$alkynyl, $C_{1-10}$-alkoxy, $C_{1-10}$alkoxycarbonyl, $C_{1-10}$-alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$-alkyl)$_2$carbamoyl, $C_{1-10}$alkylS(O)$_a$ wherein a is 0 to 2, N—($C_{1-10}$alkyl)sulphamoyl, N,N—($C_{1-10}$-alkyl)$_2$sulphamoyl, N—($C_{1-10}$alkyl)sulphamoylamino, N,N—($C_{1-10}$alkyl)$_2$sulphamoylamino, $C_{1-10}$-alkoxycarbonylamino, carbocyclyl, carbocyclyl$C_{1-10}$-alkyl, heterocyclic group, heterocyclyl$C_{1-10}$-alkyl, carbocyclyl-($C_{1-10}$-alkylene)$_e$-$R^{32}$—($C_{1-10}$-alkylene)$_f$- or heterocyclyl-($C_{1-10}$alkylene)$_g$-$R^{33}$—($C_{1-10}$ alkylene)$_h$-; wherein $R^{13}$ may be optionally substituted on carbon by one or more substituents selected from $R^{36}$; and wherein if said heterocyclyl contains an —NH— group, that nitrogen may be optionally substituted by a group selected from $R^{37}$; or $R^{13}$ is a group of formula (BIB):

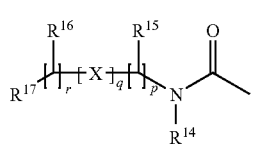

(BIB)

wherein:

X is —N($R^{38}$)—, —N($R^{38}$)C(O)—, —O—, and —S(O)$_a$—; wherein a is 0-2 and $R^{38}$ is hydrogen or $C_{1-4}$alkyl;

$R^{14}$ is hydrogen or $C_{1-4}$alkyl;

$R^{15}$ and $R^{16}$ are independently selected from hydrogen, halo, nitro, cyano, hydroxy, amino, carbamoyl, mercapto, sulphamoyl, $C_{1-6}$alkyl, $C_{2-6}$alkenyl, $C_{2-6}$alkynyl, $C_{1-6}$alkoxy, $C_{1-6}$ alkanoyl, $C_{1-6}$alkanoyloxy, N—($C_{1-6}$alkyl)amino, N,N—($C_{1-6}$ alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, carbocyclyl or heterocyclic group; wherein $R^{15}$ and $R^{16}$ may be independently optionally substituted on carbon by one or more substituents selected from $R^{41}$; and wherein if said heterocyclyl contains an —NH— group, that nitrogen may be optionally substituted by a group selected from $R^{42}$;

$R^{17}$ is selected from hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$-alkoxy, $C_{1-10}$-alkanoyl, $C_{1-10}$-alkanoyloxy, N—($C_{1-10}$alkyl)amino, N,N—($C_{1-10}$ alkyl)$_2$amino, $C_{1-10}$-alkanoylamino, N—($C_{1-10}$-alkyl)carbamoyl, $C_{1-10}$-alkoxycarbonyl, N,N—($C_{1-10}$alkyl)$_2$-carbamoyl, $C_{1-10}$-alkyl S(O)$_a$ wherein a is 0 to 2, N—($C_{1-10}$-alkyl)sulphamoyl, N,N—($C_{1-10}$alkyl)$_2$sulphamoyl, N—($C_{1-10}$-alkyl)sulphamoylamino, N,N—($C_{1-10}$alkyl)$_2$sulphamoylamino, carbocyclyl, carbocyclyl$C_{1-10}$-alkyl, heterocyclic group, heterocyclyl$C_{1-10}$-alkyl, carbocyclyl-($C_{1-10}$-alkylene)$_e$-$R^{43}$—($C_{1-10}$-alkylene)$_f$- or heterocyclyl-($C_{1-10}$ alkylene)$_g$-$R^{44}$—($C_{1-10}$alkylene)$_h$-; wherein $R^{17}$ may be optionally substituted on carbon by one or more substituents selected from $R^{47}$; and wherein if said heterocyclyl contains an —NH— group, that nitrogen may be optionally substituted by a group selected from $R^{48}$; or $R^{17}$ is a group of formula (BIC):

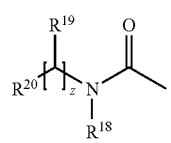

(BIC)

wherein:

$R^{18}$ is selected from hydrogen or $C_{1-4}$alkyl;

$R^{19}$ is selected from hydrogen, halo, nitro, cyano, hydroxy, amino, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$ alkyl)$_2$sulphamoyl, carbocyclyl or heterocyclic group; where $R^{19}$ may be independently optionally substituted on carbon by one or more substituents selected from $R^{51}$; and wherein if said heterocyclyl contains an —NH— group, that nitrogen may be optionally substituted by a group selected from $R^{52}$;

$R^{20}$ is selected from halo, nitro, cyano, hydroxy, amino, carbamoyl, mercapto, sulphamoyl, hydroxyaminocarbonyl, $C_{1-10}$-alkyl, $C_{2-10}$alkenyl, $C_{2-10}$alkynyl, $C_{1-10}$-alkoxy, $C_{1-10}$alkoxycarbonyl, $C_{1-10}$alkanoyl, $C_{1-10}$-alkanoyloxy, N—($C_{1-10}$alkyl)amino, N,N—($C_{1-10}$alkyl)$_2$amino, N,N,N—($C_{1-10}$-alkyl)$_3$ammonio, $C_{1-10}$-alkanoylamino, N—($C_{1-10}$-alkyl)carbamoyl, N,N—($C_{1-10}$-alkyl)$_2$carbamoyl, $C_{1-10}$-alkylS(O)$_a$, wherein a is 0 to 2, N—($C_{1-10}$alkyl)sulphamoyl, N,N—($C_{1-10}$alkyl)$_2$sulphamoyl, N—($C_{1-10}$-alkyl)sulphamoylamino, N,N—($C_{1-10}$-alkyl)$_2$sulphamoylamino, $C_{1-10}$alkoxycarbonylamino, carbocyclyl, carbocyclyl$C_{1-10}$-alkyl, heterocyclic group, heterocyclyl$C_{1-10}$-alkyl, carbocyclyl-($C_{1-10}$-alkylene)$_e$-$R^{53}$—($C_{1-10}$alkylene)$_f$- or heterocyclyl-($C_{1-10}$-alkylene)$_g$-$R^{54}$—($C_{1-10}$alkylene)$_h$-; wherein $R^{20}$ may be independently optionally substituted on carbon by one or more $R^{57}$; and wherein if said heterocyclyl contains an —NH— group, that nitrogen may be optionally substituted by a group selected from $R^{58}$;

p is 1-3; wherein the values of $R^{15}$ may be the same or different;

q is 0-1;

r is 0-3; wherein the values of $R^{16}$ may be the same or different;

m is 0-2; wherein the values of $R^{12}$ may be the same or different;

n is 1-2; wherein the values of $R^8$ may be the same or different;

z is 0-3; wherein the values of $R^{19}$ may be the same or different;

$R^{21}$ is selected from hydrogen or $C_{1-6}$alkyl;

$R^{22}$ and $R^{23}$ are independently selected from hydrogen, hydroxy, amino, mercapto, $C_{1-6}$alkyl, N—($C_{1-6}$alkyl)amino, N,N—($C_{1-6}$alkyl)$_2$amino, $C_{1-6}$alkylS(O)$_a$ wherein a is 0 to 2;

$R^{24}$ is selected from hydrogen, hydroxy, $C_{1-6}$alkyl, $C_{1-4}$alkoxy and $C_{1-6}$alkanoyloxy;

$R^{25}$ is selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^{25}$, may be independently optionally substituted on carbon by one or more $R^{67}$;

$R^{26}$, $R^{28}$, $R^{30}$, $R^{36}$, $R^{41}$, $R^{47}$, $R^{51}$ and $R^{57}$ are independently selected from halo, nitro, cyano, hydroxy, amino, carbamoyl, mercapto, sulphamoyl, hydroxyaminocarbonyl, $C_{1-10}$alkenyl, $C_{2-10}$alkyenyl, $C_{1-10}$-alkoxy, $C_{1-10}$-alkanoyl, $C_{1-10}$alkanoyloxy, $C_{1-10}$alkoxycarbonyl, N—($C_{1-10}$-alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$-alkylS(O)$_a$ wherein a is 0 to 2, N—($C_{1-10}$-alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$ sulphamoylamino, $C_{1-10}$-alkoxycarbonylamino, carbocyclyl, carbocyclyl$C_{1-10}$-alkyl, heterocyclic group, heterocyclyl$C_{1-10}$ alkyl, carbocyclyl-($C_{1-10}$-alkylene)$_e$-R$^{59}$—($C_{1-10}$-alkylene)$_f$- or heterocyclyl-($C_{1-10}$-alkylene)$_g$-R$^{60}$—($C_{1-10}$alkylene)$_h$; wherein R$^{26}$, R$^{28}$, R$^{30}$, R$^{36}$, R$^{41}$, R$^{47}$, R$^{51}$ and R$^{57}$ may be independently optionally substituted on carbon by one or more R$^{63}$; and wherein if said heterocyclyl contains an —NH— group, that nitrogen may be optionally substituted by a group selected from R$^{64}$;

R$^{27}$, R$^{29}$, R$^{31}$, R$^{37}$, R$^{42}$, R$^{48}$, R$^{52}$, R$^{58}$ and R$^{64}$ are independently selected from $C_{1-6}$alkyl, $C_{1-6}$alkanoyl, $C_{1-4}$alkylsulphonyl, sulphamoyl, N—($C_{1-6}$alkyl)sulphamoyl, N,N—($C_{1-6}$ alkyl)$_2$sulphamoyl, $C_{1-6}$alkoxycarbonyl, carbamoyl, N—($C_{1-6}$alkyl)carbamoyl, N,N—($C_{1-6}$alkyl)$_2$-carbamoyl, benzyl, phenethyl, benzoyl, phenylsulphonyl and phenyl; R$^{32}$, R$^{33}$, R$^{43}$, R$^{44}$, R$^{53}$, R$^{54}$, R$^{59}$ and R$^{60}$ are independently selected from —O—, —NR$^{65}$—, —S(O)$_x$—, —NR$^{65}$C(O)NR$^{66}$—, —NR$^{65}$C(S)NR$^{66}$—, —OC(O)N═C—, —NR$^{65}$C(O)— or —C(O)NR$^{65}$—; wherein R$^{65}$ and R$^{66}$ are independently selected from hydrogen or $C_{1-6}$alkyl, and x is 0-2;

R$^{63}$ and R$^{67}$ are independently selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl; and e, f, g and h are independently selected from 0-2;

or a pharmaceutically acceptable salt, solvate, solvate of such a salt or a prodrug thereof.

Additional suitable IBAT inhibitors having the above structure for use in combination with compounds of the present invention are selected from any one of:

(+/−)-trans-1,1-dioxo-3-ethyl-3-butyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,4-benzothiazepine;

(+/−)-trans-1,1-dioxo-3-ethyl-3-butyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,4-benzothiazepine;

1,1-dioxo-3-ethyl-3-butyl-4-hydroxy-5-phenyl-7-(N-{α-[N-(2-(S)-3-(R)-4-(R)-5-(R)-2,3,4,5,6-pentahydroxyhexyl)carbamoyl]-2-fluorobenzyl}carbamoylmethylthio)-2,3,4,5-tetrahydrobenzothiapine; or 1,1-dioxo-3-butyl-3-ethyl-4-hydroxy-5-phenyl-7-(N-{1-[N'-(2-(S)-3-(R)-4-(R)-5-(R)-2,3,4,5,6-pentahydroxyhexyl)carbamoyl]-1-(cyclohexyl)methyl}carbamoylmethylthio)-2,3,4,5-tetrahydrobenzothiepine.

Compounds of formula (AI) and (BI) or a pharmaceutically acceptable salt, solvate, solvate of such a salt or a prodrug thereof may be prepared by processes known in the art.

In a particular aspect of the invention an IBAT inhibitor or a pharmaceutically acceptable salt, solvate, solvate of such a salt or a prodrug thereof is an IBAT inhibitor or a pharmaceutically acceptable salt thereof.

Therefore in an additional feature of the invention, there is provided a combination of a compound of formula (I), or a pharmaceutically acceptable salt, solvate, solvate of such a salt or a prodrug thereof and an IBAT inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an IBAT inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;

b) an IBAT inhibitor, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) an IBAT inhibitor, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof, in the manufacture of a medicament for use in the production of a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an IBAT inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, the compound of formula (I), or a pharmaceutically acceptable salt, solvate, solvate of such a salt or a prodrug thereof, may be administered in association with a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, WO03/051821, WO03/051822, WO03/051826, PCT/GB03/02584, PCT/GB03/02591, PCT/GB03/02598, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference.

Particularly a PPAR alpha and/or gamma agonist refers to WY-14643, clofibrate, fenofibrate, bezafibrate, GW 9578, troglitazone, pioglitazone, rosiglitazone, eglitazone, proglitazone, NN622/Ragaglitazar, BMS 298585, BRL-49634, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{4-methanesulphonyloxyphenyl}ethoxy)phenyl]propanoic acid and pharmaceutically acceptable salts thereof.

Therefore in an additional feature of the invention, there is provided a combination of a compound of formula (I), or a pharmaceutically acceptable salt, solvate, solvate of such a salt or a prodrug thereof and a PPAR alpha and/or gamma agonist, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;

b) a PPAR alpha and/or gamma agonist, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) a PPAR alpha and/or gamma agonist, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in the manufacture of a medicament for use in producing a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, the compound of formula (I), or a pharmaceutically acceptable salt, solvate, solvate of such a salt or a prodrug thereof, may be administered in association with a nicotinic acid derivative or a pharmaceutically acceptable salt, solvate, solvate of such a salt or a prodrug thereof. As used herein "nicotinic acid derivative" means a compounds comprising a pyridine-3-carboxylate structure or a pyrazine-2-carboxylate structure. Examples of nicotinic acid derivatives include nicotinic acid, niceritrol, nicofuranose, NIASPAN® and acipimox.

Therefore, in an additional feature of the invention, there is provided a combination of a compound of formula (I), or a pharmaceutically acceptable salt, solvate, solvate of such a salt or a prodrug thereof and a nicotinic acid derivative or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a nicotinic acid derivative, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a nicotinic acid derivative, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a nicotinic acid derivative, or a pharmaceutically acceptable salt, solvate, solvate of such a salt or a prodrug thereof, in the manufacture of a medicament for use in the production of a cholesterol lowering effect in a warm-blooded animal, such as man.

In another aspect of the invention, the compound of formula (I), or a pharmaceutically acceptable salt, solvate, solvate of such a salt or a prodrug thereof, may be administered in association with a bile acid sequestrant or a pharmaceutically acceptable salt, solvate, solvate of such a salt or a prodrug thereof. Suitable bile acid sequestrants include cholestyramine, cholestipol and cosevelam hydrochloride.

Therefore, in an additional feature of the invention, there is provided a combination of a compound of formula (I), or a pharmaceutically acceptable salt, solvate, solvate of such a salt or a prodrug thereof and a bile acid sequestrant or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid sequestrant, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in the manufacture of a medicament for use in the production of a cholesterol lowering effect in a warm-blooded animal, such as man.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from Group X:

an antihypertensive compound (for example althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzemine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate and bevantolol hydrochloride);

an angiotensin converting enzyme inhibitor (for example alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabicriprilat, zofenopril and zofenoprilat);

an angiotensin II receptor antagonist (for example candesartan, candesartan cilexetil, losartan, valsartan, irbesartan, tasosartan, telmisartan and eprosartan);

an andrenergic blocker (for example bretylium tosylate, dihydroergotamine so mesylate, phentolamine mesylate, solypertine tartrate, zolertine hydrochloride, carvedilol or labetalol hydrochloride); an alpha andrenergic blocker (for example fenspiride hydrochloride, labetalol hydrochloride, proroxan and alfuzosin hydrochloride); a beta andrenergic blocker (for example acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate and nebivolol); or a mixed alpha/beta andrenergic blocker;

an andrenergic stimulant (for example combination product of chlorothiazide and methyldopa, the combination product of methyldopa hydrochlorothiazide and methyldopa, clonidine hydrochloride, clonidine, the combination product of chlorthalidone and clonidine hydrochloride and guanfacine hydrochloride);

channel blocker, for example a calcium channel blocker (for example clentiazem maleate, amlodipine besylate, isradipine, nimodipine, felodipine, nilvadipine, nifedipine, teludipine hydrochloride, diltiazem hydrochloride, belfosdil, verapamil hydrochloride or fostedil);

a diuretic (for example the combination product of hydrochlorothiazide and spironolactone and the combination product of hydrochlorothiazide and triamterene);

anti-anginal agents (for example amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen or verapamil hydrochloride);

vasodilators for example coronary vasodilators (for example fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexyline maleate, prenylamine, propatyl nitrate, terodiline hydrochloride, tolamolol and verapamil);

anti-coagulants (selected from argatroban, bivalirudin, dalteparin sodium, desirudin, dicumarol, lyapolate sodium, nafamostat mesylate, phenprocoumon, tinzaparin sodium and warfarin sodium);

antithrombotic agents (for example anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab and zolimomab aritox);

fibrinogen receptor antagonists (for example roxifiban acetate, fradafiban, orbofiban, lotrafiban hydrochloride, tirofiban, xemilofiban, monoclonal antibody 7E3 and sibrafiban)

platelet inhibitors (for example cilostezol, clopidogrel bisulfate, epoprostenol, epoprostenol sodium, ticlopidine hydrochloride, aspirin, ibuprofen, naproxen, sulindae, indomethacin, mefenamate, droxicam, diclofenac, sulfinpyrazone and piroxicam, dipyridamole);

platelet aggregation inhibitors (for example acadesine, beraprost, beraprost sodium, ciprostene calcium, itezigrel, lifarizine, lotrafiban hydrochloride, orbofiban acetate, oxagrelate, fradafiban, orbofiban, tirofiban and xemilofiban)

hemorrheologic agents (for example pentoxifylline);

lipoprotein associated coagulation inhibitors;

Factor VIIa inhibitors;

Factor Xa inhibitors;

low molecular weight heparins (for example enoxaparin, nardroparin, dalteparin, certroparin, parnaparin, reviparin and tinzaparin);

squalene synthase inhibitors;

squalene epoxidase inhibitors;

liver X receptor (LXR) agonists for example GW-3965 and those described in WO00224632, WO00103705, WO02090375 and WO00054759 (claim 1 and the named examples of these four application are incorporated herein by reference);

microsomal triglyceride transfer protein inhibitors for example implitapide and those described in WO03004020, WO03002533, WO02083658 and WO 00242291 (claim 1 and the named examples of these four application are incorporated herein by reference);

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Therefore, in an additional feature of the invention, there is provided a combination of a compound of formula (I), or a pharmaceutically acceptable salt, solvate, solvate of such a salt or a prodrug thereof and a compound from Group X or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a compound from Group X, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in the manufacture of a medicament for use in the production of a cholesterol lowering effect in a warm-blooded animal, such as man.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of cholesterol absorption in laboratory animals such as cats, dogs, rabbits, monkeys, rats and mice, as part of the search for new therapeutic agents.

Many of the intermediates described herein are novel and are thus provided as a further feature of the invention. For example compounds of formula (VI) show cholesterol absorption inhibitory activity when tested in the above referenced in vitro test assay and are thus claimed as a further feature of the invention.

Thus in a further feature of the invention, there is provided a compound of formula (VI), or a pharmaceutically acceptable salt, solvate, solvate of such a salt or a prodrug thereof, with the proviso that said compound is not 3-(R)-4-(R)-1-(phenyl)-3-[2-(4-fluorophenyl)-2-hydroxyethylsulphanyl]-4-{4-[N-(carboxymethyl)carbamoylmethoxy]phenyl}azetidin-2-one.

Therefore according to a further aspect of the invention there is provided a pharmaceutical composition which comprises a compound of formula (VI), or a pharmaceutically acceptable salt, solvate, solvate of such a salt or a prodrug thereof in association with a pharmaceutically-acceptable diluent or carrier, with the proviso that said compound is not 3-(R)-4-(R)-1-(phenyl)-3-[2-(4-fluorophenyl)-2-hydroxyethylsulphanyl]-4-{4-[N-(carboxymethyl)carbamoylmethoxy]phenyl}azetidin-2-one.

According to an additional aspect of the present invention there is provided a compound of the formula (VI), or a pharmaceutically acceptable salt, solvate, solvate of such a salt or a prodrug thereof, for use in a method of prophylactic or therapeutic treatment of a warm-blooded animal, such as man, with the proviso that said compound is not 3-(R)-4-(R)-

1-(phenyl)-3-[2-(4-fluorophenyl)-2-hydroxyethylsulphanyl]-4-{4-[N-(carboxymethyl) carbamoylmethoxy]phenyl}azetidin-2-one.

Thus according to this aspect of the invention there is provided a compound of the formula (VI), or a pharmaceutically acceptable salt, solvate, solvate of such a salt or a prodrug thereof, for use as a medicament, with the proviso that said compound is not 3-(R)-4-(R)-1-(phenyl)-3-[2-(4-fluorophenyl)-2-hydroxyethylsulphanyl]-4-{4-[N-(carboxymethyl) carbamoylmethoxy]phenyl}azetidin-2-one.

According to another feature of the invention there is provided the use of a compound of the formula (VI), or a pharmaceutically acceptable salt, solvate, solvate of such a salt or a prodrug thereof, in the manufacture of a medicament for use in the production of a cholesterol absorption inhibitory effect in a warm-blooded animal, such as man, with the proviso that said compound is not 3-(R)-4-(R)-1-(phenyl)-3-[2-(4-fluorophenyl)-2-hydroxyethylsulphanyl]-4-{4-[N-(carboxymethyl)carbamoylmethoxy]phenyl}azetidin-2-one.

According to another feature of the invention there is provided the use of a compound of the formula (VI), or a pharmaceutically acceptable salt, solvate, solvate of such a salt or a prodrug thereof, in the manufacture of a medicament for use in the treatment of hyperlipidaemic conditions in a warm-blooded animal, such as man, with the proviso that said compound is not 3-(R)-4-(R)-1-(phenyl)-3-[2-(4-fluorophenyl)-2-hydroxyethylsulphanyl]-4-{4-[N-(carboxymethyl) carbamoylmethoxy]phenyl}azetidin-2-one.

According to a further feature of this aspect of the invention there is provided a method for producing a cholesterol absorption inhibitory effect in a warm-blooded animal, such as man, in need of such treatment which comprises administering to said animal an effective amount of a compound of formula (VI), or a pharmaceutically acceptable salt, solvate, solvate of such a salt or a prodrug thereof, with the proviso that said compound is not 3-(R)-4-(R)-1-(phenyl)-3-[2-(4-fluorophenyl)-2-hydroxyethylsulphanyl]-4-{4-[N-(carboxymethyl)carbamoylmethoxy]phenyl}azetidin-2-one.

According to a further feature of this aspect of the invention there is provided a method of treating hyperlipidemic conditions in a warm-blooded animal, such as man, in need of such treatment which comprises administering to said animal an effective amount of a compound of formula (VI), or a pharmaceutically acceptable salt, solvate, solvate of such a salt or a prodrug thereof, with the proviso that said compound is not 3-(R)-4-(R)-1-(phenyl)-3-[2-(4-fluorophenyl)-2-hydroxyethylsulphanyl]-4-{4-[N-(carboxymethyl) carbamoylmethoxy]phenyl}azetidin-2-one.

In the above other pharmaceutical composition, process, method, use and medicament manufacture features, the alternative and preferred embodiments of the compounds of the invention described herein also apply.

EXAMPLES

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) all reactions were carried out under an inert atmosphere at ambient temperature, typically in the range 18-25° C., with solvents of HPLC grade under anhydrous conditions, unless otherwise stated;

(iii) column chromatography (by the flash procedure) was performed on Silica gel 40-63 μm (Merck);

(iv) yields are given for illustration only and are not necessarily the maximum attainable;

(v) the structures of the end products of the formula (I) were generally confirmed by nuclear (generally proton) magnetic resonance (NMR) and mass spectral techniques; magnetic resonance chemical shift values were measured in deuterated $CDCl_3$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer unless otherwise stated data was recorded at 400 MHz; and peak multiplicities are shown as follows: s, singlet; d, doublet; dd, double doublet; t, triplet; tt, triple triplet; q, quartet; tq, triple quartet; m, multiplet; br, broad; ABq, AB quartet; ABd, AB doublet, ABdd, AB doublet of doublets; dABq, doublet of AB quartets; LCMS were recorded on a Waters ZMD, LC, column xTerra MS $C_8$(Waters), detection with a HP 1100 MS-detector diode array equipped; mass spectra (MS) (loop) were recorded on VG Platform II (Fisons Instruments) with a HP-1100 MS-detector diode array equipped; unless otherwise stated the mass ion quoted is $(MH^+)$; unless further details are specified in the text, analytical high performance liquid chromatography (HPLC) was performed on Prep LC 2000 (Waters), Cromasil $C_8$, 7 μm, (Akzo Nobel); MeCN and de-ionised water 10 mM ammonium acetate as mobile phases, with suitable composition;

(vii) intermediates were not generally fully characterised and purity was assessed by thin layer chromatography (TLC), HPLC, infra-red (IR), MS or NMR analysis;

(viii) where solutions were dried sodium sulphate was the drying agent; and (ix) the following abbreviations may be used hereinbefore or hereinafter:—

| | |
|---|---|
| DCM | dichloromethane; |
| DMF | N,N-dimethylformamide; |
| TBTU | o-Benzotriazol-1-yl-N,N,N',N'-tetramethyluronium tetrafluoroborate; |
| EtOAc | ethyl acetate; |
| MeCN | acetonitrile; |
| TFA | trifluoroacetic acid; |
| DMAP | 4-(dimethylamino)pyridine; |
| BSA | N,O-Bis(trimethylsilyl)acetamide; and |
| TBAF | tetrabutylammonium fluoride. |

Example 1

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-D-valine N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-D-valine The diastereomers of N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-valine were partly separated on a Kromasil C8-column using 35% MeCN in 0.1M ammonium acetate buffer as eluent.

First diastereomer eluated and analyzed on a Chiralpak AD column (10μ, 4.6*250 mm, 1 mL/min, mobile phase:Heptane/Isopropanol/Formic acid 65/35/0.1) at 254.00 nm to give a d.e=68%. Retention time at 26.44.

Example 2

1-[(N-{[4-((2R,3R)-1-(4-chlorophenyl)-3-{[(2R or S)-2-(4-chlorophenyl)-2-hydroxyethyl]thio}-4-oxoazetidin-2-yl)phenoxy]acetyl}glycyl)amino]cyclopropanecarboxylic acid To a 30° C. solution of N-{[4-((2R,3R)-1-(4-chlorophenyl)-3-{[2-(4-chlorophenyl)-2-oxoethyl]thio}-4-oxoazetidin-2-yl)phenoxy]acetyl}glycine (0.030 g, 0.052 mmol and N-methylmorpholine (0.016 g, 0.157 mmol) in $CH_2Cl_2$ (5 ml) was added TBTU (0.020 g, 0.063 mmol). After 1 h, 1-amino-1-cyclopropanecarboxylic acid (0.006 g, 0.063 mmol) was added. After 1 h, the reaction was quenched by the addition of water (1 ml). The reaction mixture was concentrated and to the residue was added MeOH (3 ml) and $NaBH_4$ (0.020 g, 0.523 mmol). Full conversion to the corresponding alcohol was achieved after 5 minutes. The reaction was quenched by the addition of 0.1M $NH_4OAc$ buffer (1 ml) followed by concentration. The residue was purified through preparative HPLC using an eluent of 0-50% $CH_3CN$ in 0.1M $NH_4OAc$ buffer. This gave separation of the two diastereomers (epimers at the benzylic alcohol position). Freeze drying of each of the two fractions afforded the individual pure diastereomers as colourless solids (combined yield 0.008 g, 23%). First eluting fraction: $^1H$ NMR [$(CD_3)_2SO$], 400 MHz] δ 0.90-0.93 (m, 2H), 1.19-1.26 (m, 2H), 2.89-2.92 (m, 2H), 3.69-3.71 (m, 2H), 4.26-4.29 (m, 1H), 4.51 (s, 2H), 4.69-4.74 (m, 1H), 5.05-5.07 (m, 1H), 6.98 (d, 2H), 7.20 (d, 2H), 7.30-7.38 (m, 8H), 7.78-7.82 (m, 1H), 8.17-8.22 (m, 1H). second eluting fraction: $^1H$ NMR [$(CD_3)_2SO$], 400 MHz] δ 0.89-0.92 (m, 2H), 1.20-1.25 (m, 2H), 2.88-2.90 (m, 2H), 3.68-3.71 (m, 2H), 4.28-4.31 (m, 1H), 4.47-4.51 (m, 2H), 4.71-4.75 (m, 1H), 5.02-5.04 (m, 1H), 6.98 (d, 2H), 7.17-7.36 (m, 10H), 7.79-7.83 (m, 1H), 8.18-8.21 (m, 1H).

Example 3

N-{[4-((2R,3R)-1-(4-fluorophenyl)-3-{[(2R or 6)-2-(4-fluorophenyl)-2-hydroxyethyl]thio}-4-oxoazetidin-2-yl)phenoxy]acetyl}glycyl-3-methyl-D-valine To a solution of N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycine (0.19 g, 0.35 mmol) in DMF (5 ml) under an atmosphere of nitrogen was added N-methyl morpholine (0.12 g, 1.23 mmol) followed by the addition of TBTU (0.15 g, 0.46 mmol). After 1 h, 3-methyl-D-valine (0.064 g, 0.49 mmol) was added. After 30 minutes, the reaction was quenched by the addition of water (1 ml). After an additional 15 minutes, the reaction mixture was purified through preparative HPLC using an eluent of 10-50% $CH_3CN$ in 0.1M $NH_4OAc$ buffer. Freeze drying of pure fractions afforded the desired compound (0.17 g, 74%) as a colourless solid. $^1H$ NMR [$(CD_3)_2SO$], 400 MHz] δ 0.90 (s, 9H), 2.91 (d, 2H), 3.84 (d, 2H), 4.11 (d, 1H), 4.25 (d, 1H), 4.51 (s, 2H), 4.70 (t, 1H), 5.06 (d, 1H), 5.63 (s, br, 1H), 6.97-7.37 (m, 12H), 7.91-7.94 (m, 1H), 8.23 (t, 1H).

Example 4

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-3-cyclohexyl-D-alanine To a solution of N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycine (0.14 g, 0.26 mmol) in DMF (4 ml) under an atmosphere of nitrogen was added N-methyl morpholine (0.091 g, 0.90 mmol) followed by the addition of TBTU (0.108 g, 0.34 mmol). After 1 h, 3-cyclohexyl-D-alanine (0.062 g, 0.36 mmol) was added. After 30 minutes, the reaction was quenched by the addition of water (1 ml). After an additional 15 minutes, the reaction mixture was purified through preparative HPLC using an eluent of 10-50% $CH_3CN$ in 0.1M $NH_4OAc$ buffer. Freeze drying of pure fractions afforded the desired compound (0.093 g, 52%) as a colourless solid. $^1H$ NMR [$(CD_3)_2SO$], 400 MHz] δ 0.76-1.67 (m, 13H), 2.89-2.93 (m, 2H), 3.76 (d, 2H), 4.15-4.21 (m, 1H), 4.26 (d, 1H), 4.51 (s, 2H), 4.70 (t, 1H), 5.06 (d, 1H), 6.97-7.37 (m, 12H), 8.01 (d, 1H), 8.22 (t, 1H).

Example 5

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-β,β-dimethyl-D-phenylalanine To a solution of N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycine (0.020 g, 0.037 mmol) in DMF (2 ml) under an atmosphere of nitrogen was added N-methyl morpholine (0.015 g, 0.147 mmol) followed by the addition of TBTU (0.015 g, 0.048 mmol). After 1 h, β,β-dimethyl-D-phenylalanine trifluoroacetate salt (0.016 g, 0.052 mmol) was added. After 30 minutes, the reaction was quenched by the addition of water (1 ml). After an additional 15 minutes, the reaction mixture was purified through preparative HPLC using an eluent of 10-50% $CH_3CN$ in 0.1M $NH_4OAc$ buffer. Freeze drying of pure fractions afforded the desired compound (0.020 g, 76%) as a colourless solid. $^1H$ NMR [$(CD_3)_2SO$], 400 MHz] δ 1.28 (s, 3H), 1.30 (s, 3H), 2.88-2.93 (m, 2H), 3.62 (dd, 1H), 3.78 (dd, 1H), 4.28 (d, 1H), 4.49 (s, 2H), 4.50 (d, 1H), 4.71 (t, 1H), 5.05 (d, 1H), 6.94-7.35 (m, 17H), 7.66 (d, 1H), 8.22 (t, 1H).

Example 6

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-D-lysine N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-$N^6$-[(9H-fluoren-9-ylmethoxy)carbonyl]-D-lysine (0.010 g, 0.011 mmole) was dissolved in 0.5 mL of piperidine in DMF (23% by volume). After 5 minutes the solvent was removed under reduced pressure and the residue was purified by preparative HPLC on a Kromasil C8-column using a gradient of 5-100% MeCN in 0.1M ammonium acid buffer as eluent. After removing the solvent under reduced pressure and freeze-drying from water, 0.0065 g (86%) of the desired product was obtained.

NMR (500 MHz, CD$_3$COOD) 1.36-1.47 (m, 2H), 1.60-1.76 (m, 3H), 1.86-1.96 (m, 1H), 2.87-2.94 (m, 2H), 2.97-3.09 (m, 2H), 3.97 (ABq, 2H), 4.05 (d, 1H), 4.29 (dd, 1H), 4.64 (s, 2H), 4.81-4.87 (m, 1H), 4.93 (d, 1H), 6.99-7.06 (m, 4H), 7.06-7.11 (m, 2H), 7.28-7.32 (m, 2H), 7.34-7.40 (m, 4H)

Preparation of Starting Materials for the Above Examples

Methods

Method 1

N-{[4-((2R,3R)-1-(4-chlorophenyl)-3-{[2-(4-chlorophenyl)-2-oxoethyl]thio}-4-oxoazetidin-2-yl)phenoxy]acetyl}glycine To a stirred solution of [4-((2R,3R)-1-(4-chlorophenyl)-3-{[2-(4-chlorophenyl)-2-oxoethyl]thio}-4-oxoazetidin-2-yl) phenoxy]acetic acid, 302.1 mg, 0.585 mmol) in DCM (6 ml) were added N-methylmorpholine (190 µl, 1.728 mmol) and tert-butyl glycinate hydrochloride (133.4 mg, 0.80 mmol). After 10 minutes TBTU (224.3 mg, 0.67 mmol) was added and the reaction mixture was stirred at ambient temperature for 60 hours. The intermediate tert-butylester of the title compound was confirmed. M/z: 626.88 (M−H). DCM (10 ml) and water (15 ml) were added and the mixture was acidified to pH of 3 with KHSO$_4$ (2M). The organic phase was washed with water (2×15 ml), the combined water phases were extracted with DCM (10 ml), dried over Na$_2$SO$_4$, filtered and the solvent was evaporated off. A solution of the residue (500 mg) in DCM (10 ml) and TFA (4 ml) was stirred at ambient temperature overnight. The solvent was removed under reduced presssure, toluene was used to assist the removal of TFA. The residue was purified with preparative HPLC on a C8 column. A gradient from 20 to 50% MeCN in 0.1M ammonium acetate buffer was used as eluent. After lyophilisation, the title compound was obtained as a white solid (166.9 mg, 50%). $^1$H-NMR (400 MHz, DMS-d$_6$): 3.51 (d, 2H), 4.33 (d, 1H), 4.34 (s, 1H), 4.36 (s, 1H), 4.47 (s, 2H), 5.17 (d, 1H), 6.96 (d, 2H), 7.16-7.21 (m, 2H), 7.35 (d, 4H), 7.54-7.59 (m, 2H), 7.83-7.90 (brs, 1H), 7.91-7.95 (m, 2H). M/z: 571.04 (M−H) and 572.88 (M+H).

Method 2

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycine To a 0° C. solution of N-{[4-((2R,3R)-1-(4-fluorophenyl)-3-{[2-(4-fluorophenyl)-2-oxoethyl]thio}-4-oxoazetidin-2-yl)phenoxy]acetyl}glycine (1.10 g, 2.04 mmol)) in MeOH (20 ml) was added in small portions NaBH$_4$ (0.154 g, 4.07 mmol). The reaction was then allowed to reach room temperature. After 5 minutes full conversion to the corresponding alcohol was obtained: The reaction was quenched by the addition of 0.1M NH$_4$OAc buffer (3 ml) followed by concentration of the reaction mixture. The crude two diastereomeric alcohols (epimeric at the benzylic alcohol position) were separated through preparative HPLC using an eluent of 20-35% CH$_3$CN in 0.1M NH$_4$OAc buffer. The first eluting fraction was collected and freeze dried. This yielded the desired diastereomer (0.40 g, 36%) as a colourless solid. 1H NMR analysis confirmed that this diastereomer was of >95:5 dr. m/z: 541.5 (M−1). $^1$H NMR [(CD$_3$)$_2$SO], 400 MHz] δ 2.90 (d, 2H), 3.78 (d, 2H), 4.25 (d, 1H), 4.52 (s, 2H), 4.67-4.73 (m, 1H), 5.06 (d, 1H), 6.97-7.38 (m, 12H), 8.35 (t, 1H).

Method 3

β,β-dimethyl-D-phenylalanine trifluoroacetate salt

Commercially available N-(tert-butoxycarbonyl)-β,β-dimethyl-D-phenylalanine-2-methylpropan-2-amine salt (1:1) (1.0 g, 2.73 mmol) was dissolved in CH$_2$Cl$_2$ (50 ml) followed by the addition of 1M HCl (aq. 100 ml). The aqueous phase was extracted with CH$_2$Cl$_2$ (50 ml). The pooled organic phase was dried (MgSO$_4$) and concentrated. To the residue was added CH$_2$Cl$_2$ (4 ml) and TFA (3 ml). After 2 h, the reaction mixture was concentrated to give the desired compound (0.83 g, 99%) as a colourless solid. $^1$H NMR (D$_2$O, 400 MHz) δ 1.38 (s, 3H), 1.45 (s, 3H), 4.17 (s, 1H), 7.26-7.42 (m, 5H).

Examples of Intermediates of Formula (VI)

Method 4

N-{[4-((2R,3R)-1-(4-fluorophenyl)-3-{[2-(4-fluorophenyl)-2-hydroxyethyl]thio}-4-oxoazetidin-2-yl)phenoxy]acetyl}-D-alanine N-{[4-((2R,3R)-1-(4-fluorophenyl)-3-{[2-(4-fluorophenyl)-2-oxoethyl]thio}-4-oxoazetidin-2-yl)phenoxy]acetyl}-D-alanine was dissolved in methanol (1.5 ml) whereafter sodium borohydride was added and the mixture was stirred for 30 minutes. After addition of ammonium acetate/H2O solution (2 ml), the methanol was evaporated and the product purified by preparative HPLC (CH3CN/0.1% ammoniumacetate 20:80-100:0). The fractions containing product confirmed by LC-MS were lyophilized and 27 mg (48%) of the desired product was obtained. m/z: 555.0 (M−1).

Method 5

N-{[4-((2R,3R)-1-(4-fluorophenyl)-3-([2-(4-fluorophenyl)-2-hydroxyethyl]thio)-4-oxoazetidin-2-yl)phenoxy]acetyl}-L-tryptophan To a solution of [4-((2R,3R)-1-(4-fluorophenyl)-3-{[2-(4-fluorophenyl)-2-oxoethyl]thio}-4-oxoazetidin-2-yl)phenoxy]acetic acid (0.050 g, 0.103 mmol) in CH$_2$Cl$_2$ (5 ml) was added Tryphtophane tert-butyl ester hydrochloride (0.037 g, 0.12 mmol) and N-Methylmorpholine (31 mg, 0.31 mmol) at room temperature under an atmosphere of nitrogen. After 10 minutes TBTU (43 mg, 0.13 mmol) was added. After 2 hours HPLC showed a 90% conversion and after 4 hours full conversion was obtained to the corresponding tert-butyl-ester. The crude ester was put on a short pad of silica gel and eluted with EtOAc/CH$_2$Cl$_2$, 25/75. Pure fractions were collected and concentrated. CH$_2$Cl$_2$ (5 ml) and TFA (1 ml) were added and the reaction was allowed to stir at room temperature for 4 hours. The resulting acid was concentrated and the remaining trace of TFA was azeotropically removed through co-evaporation with toluene (2×5 ml). To the residue was added 5 ml of MeOH followed by the addition of Sodium borohydride (0.016 g, 0.414 mmol). Full conversion to the corresponding alcohol was achieved after 5 minutes according to HPLC analysis. The reaction was quenched by the addition of 0.1M NH$_4$OAc buffer (1 ml). The volatiles were evaporated and the residue was purified through preparative HPLC (gradient 20-50% CH$_3$CN in 0.1M ammonium acetate buffer). Freeze drying of pure fractions afforded the desired product as a colourless solid (0.040 g, 58%). m/z: 670.3 (M−1). $^1$H NMR [(CD$_3$)$_2$SO], 400 MHz] δ 2.85-2.95 (m, 2H), 3.07-3.12 (m, 1H), 3.22-3.27 (m, 1H), 4.24-4.27 (m, 1H), 4.34-4.38 (m, 1H), 4.41 (s, 2H), 4.70-4.76 (m, 1H), 5.01-5.04 (m, 1H), 6.80-7.35 (m, 16H), 7.50-7.53 (m, 1H), 7.85-7.92 (m, 1H), 10.76 (s, 1H).

Method 7

$N^2$-{[4-((2R,3R)-1-(4-fluorophenyl)-3-{[2-(4-fluorophenyl)-2-hydroxyethyl]thio}-4-oxoazetidin-2-yl)phenoxy]acetyl}-L-glutamine

[4-((2R,3R)-1-(4-fluorophenyl)-3-{[2-(4-fluorophenyl)-2-oxoethyl]thio}-4-oxoazetidin-2-yl)phenoxy]acetic acid (50 mg, 0.103 mmol), tert-butyl L-glutaminate hydrochloride (30 mg, 0.124 mmol) and N-methylmorpholine (40 mg, 0.396 mmol) were dissolved in methylene chloride (1 ml). TBTU (40 mg, 0.125 mmol) was added and the mixture was stirred for 90 min at room temperature. The solvent was evaporated and the residue was dissolved in formic acid (1 ml). The mixture was heated to 45-50° C. and stirred at this temperature for 4 h. The reaction mixture was evaporated under reduced pressure. Toluene (5 ml) was added and evaporated. The residue was dissolved in methanol (1 ml). NaBH4 (30 mg, 0.793 mmol) was added and the mixture was stirred for 15 min at room temperature. Acetic acid (50 mg, 0.83 mmol) was added and the reaction mixture was evaporated under reduced pressure. The residue was purified by preparative HPLC using acetonitrile/ammonium acetate buffer (35:65) as eluent. After freeze-drying 47 mg (74%) of the title compound was obtained. $^1$H-NMR, 300 MHz, DMSO): 1.72-2.16 (m, 4H), 2.81-2.95 (m, 2H), 4.08-4.20 (m, 1H), 4.26-4.31 (m, 1H), 4.50 (s, 2H), 4.65-4.78 (m, 1H), 5.03-5.08 (m, 1H), 6.68 (s, 1H), 6.89-7.44 (m, 14H), 8.29 (d, 1H).

Method 8

N-{[4-((2R,3R)-1-(4-Fluorophenyl)-3-{[2-(4-fluorophenyl)-2-hydroxyethyl]thio}-4-oxoazetidin-2-yl)phenoxy]acetyl}-D-serine A solution of [4-((2R,3R)-1-(4-fluorophenyl)-3-{[2-(4-fluorophenyl)-2-oxoethyl]thio}-4-oxoazetidin-2-yl)phenoxy]acetic acid (0.050 g, 0.103 mmol), O-(tert-butyl)-D-Serine tert-butyl ester hydrochloride (0.032 g, 0.147 mmol) and N-Methylmorpholine (0.035 ml, 0.318 mmol) in DCM (4 ml) was stirred at RT for 5 min, after which TBTU (0.044 g, 0.137 mmol) was added. After 3 h, the conversion to the ester (m/z: 683.1) was completed and the solution was added TFA (2 ml). After 22 h, the solvent was removed under reduced pressure and the residue (m/z: 571.1) was dissolved in MeOH (4 ml). To the solution were successively added small portions of NaBH4 (totally 0.130 g, 3.44 mmol) until the reduction was completed. The reaction mixture was added a 0.1M ammonium acetate buffer (3 ml) and the methanol was removed under reduced pressure. The remaining solution was purified by preparative HPLC using a gradient of 20-60% MeCN in 0.1M ammonium acetate buffer as eluent. After freeze-drying, 0.021 g (36% yield) of the desired product (as a mixture of diastereomers) was obtained as a white solid. M/z: 573.1. $^1$H NMR (DMSO, 400 MHz): δ 2.84-2.96 (m, 2H), 3.47 (dd, 1H), 3.69 (dd, 1H), 3.97-4.06 (m, 1H), 4.27-4.32 (m, 1H), 4.52 (ABq, 2H), 4.68-4.77 (m, 1H), 5.04-5.09 (m, 1H), 5.65 (bs, 1H), 6.99 (d, 2H), 7.07-7.41 (m, 10H), 7.89 (d, 1H).

Method 9

N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-$N^6$-[(9H-fluoren-9-ylmethoxy)carbonyl]-D-lysine A mixture of N-{[4-((2R,3R)-1-(4-fluorophenyl)-3-{[(2R or 8)-2-(4-fluorophenyl)-2-hydroxyethyl]thio}-4-oxoazetidin-2-yl)phenoxy]acetyl}glycine (0.0093 g, 0.017 mmole), N-methylmorpholin (0.010 mL, 0.051 mmole) in DMF (1 mL) was stirred, TBTU (0.0077 g, 0.025 mmole) was added. The mixture was stirred for 50 minutes under $N_2$-atmosphere. $N^6$-[(9H-fluoren-9-ylmethoxy)carbonyl]-D-lysine (0.010 g, 0.025 mmole) was added and stirred for 1 hour. A small amount of water was added and the solvent was removed under reduced pressure. The residue was purified by preparative HPLC on a Kromasil C8-column using a gradient of 5-100% MeCN in 0.1M ammonium acid buffer as eluent. After removing the solvent under reduced pressure and freeze-drying from water, 0.010 g (65%) of the desired product was obtained.

M/z 893.35

Absorption

Absorption of the compounds of formula (I) was tested in a Caco-2 cells model (Gastroenterology 1989, 96, 736):

| Compound (I) | Caco value ($10^{-6}$ cm/sec) |
|---|---|
| N-{[4-((2R,3R)-1-(4-fluorophenyl)-3-{[(2R)-2-(4-fluorophenyl)-2-hydroxyethyl]thio}-4-oxoazetidin-2-yl)phenoxy]acetyl}glycyl-3-methyl-D-valine | 0.02 |
| N-{[4-((2R,3R)-1-(4-fluorophenyl)-3-{[(2R)-2-(4-fluorophenyl)-2-hydroxyethyl]thio}-4-oxoazetidin-2-yl)phenoxy]acetyl}glycyl-3-cyclohexyl-D-alanine | 0.04 |

The invention claimed is:

1. A compound which is chosen from:
N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-D-lysine; and
N-{[4-((2R,3R)-1-(4-fluorophenyl)-3-{[(2R or S)-2-(4-fluorophenyl)-2-hydroxyethyl]thio}-4-oxoazetidin-2-yl)phenoxy]acetyl}glycyl-3-cyclohexyl-D-alanine;
or a pharmaceutically acceptable salt thereof.

2. A pharmaceutical formulation comprising a compound according to claim 1 in admixture with a pharmaceutically acceptable adjuvant, diluent and/or carrier.

* * * * *